US012138167B2

(12) United States Patent
Yeo et al.

(10) Patent No.: US 12,138,167 B2
(45) Date of Patent: Nov. 12, 2024

(54) DEVICE FOR CARDIAC VALVE REPAIR AND METHOD OF IMPLANTING THE SAME

(71) Applicant: SINGAPORE HEALTH SERVICES PTE. LTD., Singapore (SG)

(72) Inventors: Khung Keong Yeo, Singapore (SG); Nicolas Daniel Marie Foin, Singapore (SG)

(73) Assignee: SINGAPORE HEALTH SERVICES PTE. LTD., Singapore (SG)

(*) Notice: Subject to any disclaimer, the term of this patent is extended or adjusted under 35 U.S.C. 154(b) by 573 days.

(21) Appl. No.: 17/461,316

(22) Filed: Aug. 30, 2021

(65) Prior Publication Data

US 2021/0386547 A1 Dec. 16, 2021

Related U.S. Application Data

(63) Continuation-in-part of application No. 16/308,782, filed as application No. PCT/SG2017/050296 on Jun. 12, 2017, now Pat. No. 11,116,635.

(30) Foreign Application Priority Data

Jun. 13, 2016 (SG) .......................... 10201604791X

(51) Int. Cl.
*A61F 2/24* (2006.01)
(52) U.S. Cl.
CPC .......... *A61F 2/2463* (2013.01); *A61F 2/2466* (2013.01); *A61F 2220/0016* (2013.01);
(Continued)

(58) Field of Classification Search
CPC ........ A61F 2/24; A61F 2/2412; A61F 2/2427; A61F 2/2433; A61F 2/2454; A61F 2/246;
(Continued)

(56) References Cited

U.S. PATENT DOCUMENTS 6,482,228 B1 * 11/2002 Norred .................. A61F 2/2418
623/1.24
11,116,635 B2 * 9/2021 Yeo ........................ A61F 2/2433
(Continued)

FOREIGN PATENT DOCUMENTS

DE 102013017750 A1 4/2015
EP 1959865 A1 8/2008
(Continued)

OTHER PUBLICATIONS

Japanese Final Office Action for Application No. JP2018-563776.
(Continued)

*Primary Examiner* — Jocelin C Tanner
(74) *Attorney, Agent, or Firm* — JCIP; Joseph G. Chu

(57) ABSTRACT

A device for cardiac valve repair, the device comprising: a stent adapted to anchor to at least one tissue site, the tissue site located upstream with respect to a heart valve of a patient; and a neo-leaflet arranged to extend from the upstream anchoring means, the neo-leaflet comprising a free end, wherein the neo-leaflet is operable to extend across the heart valve via a commissure in between two heart valve leaflets of the patient's heart and locate the free end downstream from the heart valve and the neo-leaflet operable to coapt with the heart valve leaflets of the patient's heart to prevent and/or minimize a backflow of blood. The present invention is suitable for the treatment of heart valves using minimally invasive approaches. Additionally, the present invention is directed to a method of implanting a device for cardiac valve repair in a patient's heart.

20 Claims, 14 Drawing Sheets

(52) U.S. Cl.
CPC . *A61F 2220/005* (2013.01); *A61F 2220/0066* (2013.01); *A61F 2220/0075* (2013.01)

(58) Field of Classification Search
CPC .. A61F 2/2466; A61F 2/90; A61F 2/95; A61F 2/2451; A61F 2/2463; A61F 2220/0008; A61F 2250/0003
See application file for complete search history.

(56) References Cited

U.S. PATENT DOCUMENTS

| | | | | |
|---|---|---|---|---|
| 2010/0298929 | A1* | 11/2010 | Thornton | A61F 2/246 623/2.1 |
| 2011/0184510 | A1* | 7/2011 | Maisano | A61B 17/068 623/1.24 |
| 2013/0325110 | A1* | 12/2013 | Khalil | A61F 2/2466 623/2.11 |
| 2014/0309732 | A1* | 10/2014 | Solem | A61F 2/2412 623/2.36 |

FOREIGN PATENT DOCUMENTS

| | | |
|---|---|---|
| WO | 2014114796 A1 | 7/2014 |
| WO | 2014207575 A | 12/2014 |

OTHER PUBLICATIONS

Examination Report from Intellectual Property India for Application No. 201917001003.
Office Action for Korean Application No. 10-2019-7001197.

* cited by examiner

DEVICE FOR CARDIAC VALVE REPAIR AND METHOD OF IMPLANTING THE SAME

CROSS-REFERENCE TO RELATED APPLICATIONS

This application is a continuation-in-part of U.S. patent application Ser. No. 16/308,782, which is a National Phase Application entered on Dec. 10, 2018, under 35 U.S.C. § 371 of PCT/SG2017/050296 filed on Jun. 12, 2017, which published as WO2017/217932A1 on Dec. 21, 2017, which claims the right of priority to Singapore Application No. 10201604791X filed on Jun. 13, 2016, the contents of each is incorporated herein by references to their entirety.

FIELD OF INVENTION

The invention relates to the field of implantable medical devices, in particular to cardiac valve repair devices and methods of implanting the same. The invention is suitable for transcatheter and minimally invasive heart valve treatment, in particular for repair of a non-functional tricuspid or mitral heart valve.

BACKGROUND OF INVENTION

Rationale

Tricuspid regurgitation (TR) affects millions of people worldwide. It is difficult to treat and even surgical repair can fail. Some studies have shown long term moderate to severe recurrent TR of up to 30% in patients who receive surgical repair[1]. TR can result in significant complications such as pulmonary hypertension, right heart failure, liver cirrhosis and the complications associated with right heart failure (e.g. venous ulcers). Current treatment is largely medical with the use of diuretics such as Lasix and spironolactone. There has been no randomized trial showing the superiority of one treatment option over another.

The problem with TR is that it is seldom isolated. It often occurs together with other valvular heart disease or in the presence of heart failure or pulmonary hypertension. If surgery is performed for the primary valve disease, the tricuspid valve may be repaired or replaced at the same time. However, for many patients, the development of severe TR is a late manifestation and even when the primary pathology is treated, the TR can remain a problem. This is because the right ventricle (RV) and the tricuspid annulus remodels and this seldom reverses. In other instances, the underlying pathology cannot be reversed, e.g. primary pulmonary hypertension or ischemic cardiomyopathy, but the secondary TR itself is a cause of significant morbidity and frequent hospitalization.

Clinical Need and Current Treatment Limitations

The current treatment for TR is either medical therapy or surgery. However surgery is of limited efficacy and significant risk. Recurrence after concomitantly performed with Mitral Valve (MV) surgery: 15% at 1 month, 31% at 8 years[2]; also dependent on repair technique e.g., ring annuloplasty 17%, Bicuspidization 14%[2,3]. There are current no working percutaneous models of TR repair or Tricuspid Valve (TV) replacement although it is believed that a few companies and investigators have started work in the area. Clinical studies in patients are still lacking. Current approaches aim to replace the function of the tricuspid valve by implanting a stented valve as replacement of the native valve or by implanting stented valve in the inferior vena cava and the superior vena cava. By doing so, this last method aims to obviate the problem of tricuspid regurgitation by removing the function of the right atrium. The current approaches are difficult in practice because of the large variation in tricuspid valve and vena cava anatomies. In addition, the vena cava approach is limited by the non-physiologic re-arrangement of human anatomy and does not take into account effects of high right-sided cardiac pressures, which may continue its deleterious effects on the lungs.

The prevalence of isolated TR is poorly defined but approximates 0.8% to 3.8%[4,5]. Its effects are more commonly seen in patients with underlying left sided valvular heart disease such as in mitral stenosis or mitral regurgitation, ranging from 37 to 74%[6-8]. The clinical burden of TR is clear with right-sided heart failure refractory to treatment. Patients are prone to recurrent admissions. Other than symptomatic relief, there is no drug-therapy that has been shown in randomized trials to improve long-term prognosis.

It is one objective of the present invention to provide a minimally invasive and simple approach to treat valve regurgitation and avoid limitations associated with predicate minimally invasive heart valve treatment approaches. It is another objective of the proposed present invention to be implanted without general anaesthesia and/or open heart surgery.

It is a further objective of the present invention to avoid the disadvantages associated with complete heart valve replacement devices which cannot accommodate suitably for different valve annulus sizes and may require a complex delivery systems for implantation. The proposed device according to the present invention is designed with an objective of accommodating for various valvular anatomies and diseases.

SUMMARY OF THE INVENTION

The present invention seeks to address and/or ameliorate the problems in the prior art by providing a device for cardiac valve repair that is simple, capable of accommodating different valvular anatomies and diseases and is suitable for minimally invasive implantation approaches.

According to an aspect of the present invention, there is provided a device for cardiac valve repair, the device comprising: at least one upstream anchoring means adapted to anchor to at least one tissue site, the tissue site located upstream with respect to a heart valve of a patient; and a coaptation structure arranged to extend from the upstream anchoring means, the coaptation structure comprising a free end, wherein the coaptation structure is operable to extend across the heart valve and locate the free end downstream from the heart valve and the coaptation structure operable to coapt with at least one heart valve leaflet of the patient's heart to prevent and/or minimize a backflow of blood.

The fact that the coaptation structure that is operable to extend across a heart valve to locate the free end of the coaptation structure downstream from the heart valve, allows the coaptation structure to, without hindrance and restriction (e.g. via a downstream anchor), effectively replace and/or support the coaptation function of a failing valve leaflet, and/or to act as an additional support for coaptation of the valve leaflets which are spaced further apart due to for example, annular dilatation. Locating the free end of the coaptation structure downstream from the heart valve allows for optimal efficiency in the coaptation of the coaptation structure and the valve leaflets.

Preferably, the coaptation structure is flexible.

Preferably, the coaptation structure comprises a balloon having a surface for coaptation of at least one heart valve leaflet of the patient's heart. More preferably, the balloon is expandable.

Preferably, the device further comprises a connecting means adapted to connect the upstream anchoring means and the balloon, wherein the connecting means is adapted to arrange the balloon at a first location between two or more heart valve leaflets of the patient's heart.

Preferably, the coaptation structure comprises a neo-leaflet. More preferably, the neo-leaflet comprises a means for providing structure to the neo-leaflet and wherein said means is flexible. Even more preferably, the neo-leaflet comprises a polymer, fabric, tissue or combination thereof. Preferably, the neo-leaflet is expandable.

Preferably, the device further comprises a connecting means adapted to connect the upstream anchoring means and the neo-leaflet, wherein the connecting means is adapted to arrange a portion of the neo-leaflet at a first location between two or more heart valve leaflets of the patient's heart.

Preferably, the neo-leaflet is extendable onto a surface of at least one heart valve leaflet of the patient's heart.

Preferably, at least a portion of the neo-leaflet is extendable into a commissure between two adjacent heart valve leaflets of the patient's heart.

Preferably, the device comprises a stabilizing structure adapted to extend across the heart valve of the patient, and wherein the stabilizing structure is configured to maintain the downstream location of the free end of neo-leaflet. More preferably, the stabilizing structure comprises a weighted free end.

Preferably, the stabilizing structure comprises one or more stabilizing tether adapted to connect the stabilizing structure to the neo-leaflet. More preferably, the stabilizing tether is adapted to connect to the free end of the neo-leaflet.

Preferably, the coaptation structure comprises a membrane, wherein a portion of the membrane is extendable into a commissure between two adjacent heart valve leaflets of the patient's heart.

Preferably, the upstream tissue site is a blood vessel and the upstream anchoring means is a stent.

Preferably, the heart valve is a tricuspid valve. More preferably, the stent is adapted to anchor at the coronary sinus of the patient's heart, and/or the stent is adapted to anchor at the inferior vena cava of the patient.

Preferably, the device comprises a second upstream anchoring means, wherein the second upstream anchoring means is a stent adapted to anchor at the superior vena cava of the patient.

Preferably, the heart valve is a mitral valve and the stent is adapted to anchor at a pulmonary vein of the patient's heart.

Preferably, the upstream anchoring means and the coaptation structure are separate components of the cardiac valve repair device and wherein the upstream anchoring means and the coaptation structure are configured to connect with one another, or optionally, the upstream anchoring means and the coaptation structure are a unitary structure.

Preferably, the device is crimpable or compressible for transcatheter delivery.

According to another aspect of the present invention, there is provided a method of implanting a device for cardiac valve repair in a patient's heart, the method comprising the steps of:

(a) delivering a device for cardiac valve repair to the patient's heart, the device comprising at least one upstream anchoring means and a coaptation structure arranged to extend from the upstream anchoring means;

(b) anchoring the upstream anchoring means to at least one tissue site in the patient's heart, the tissue site located upstream with respect to a heart valve of the patient's heart;

(c) deploying the coaptation structure to extend across the heart valve to locate a free end of the coaptation structure downstream from the heart valve, and for the coaptation structure to coapt with at least one heart valve leaflet of the patient's heart to prevent and/or minimize a backflow of blood.

Preferably, the upstream anchoring means and the coaptation structure are separate components and the method comprises delivering the upstream anchoring means and the coaptation structure separately to the patient's heart. More preferably, the method further comprises the step of connecting the upstream anchoring means with the coaptation structure. Even more preferably, the upstream anchoring means and the coaptation structure are connected via a connecting means.

Preferably, the method further comprises the step of testing and verifying the stability of the upstream anchoring means.

Preferably, the method comprises deploying the coaptation structure before anchoring the upstream anchoring means.

Preferably, the coaptation structure is expandable and the method further comprises the step of expanding the coaptation structure.

Preferably, the upstream anchoring means is a stent and the method comprises anchoring the stent at the coronary sinus of the right atrium of the patient's heart, and deploying the coaptation structure such that the free end of the coaptation structure extends into the right heart ventricle of the patient and the coaptation structure coapts with at least one tricuspid valve leaflet of the patient's heart.

Preferably, the upstream anchoring means is a stent and the method comprises anchoring the stent at the inferior vena cava of the patient, and deploying the coaptation structure such that the free end of the coaptation structure extends into the right heart ventricle of the patient and the coaptation structure coapts with at least one tricuspid valve leaflet of the patient's heart.

Preferably, the cardiac valve repair device comprises a second upstream anchoring means, wherein the second upstream anchoring means is a second stent and the method comprises anchoring the second stent at the superior vena cava of the patient.

Preferably, the upstream anchoring means is a stent and the method comprises anchoring the stent at a pulmonary vein of the left atrium of the patient's heart, and deploying the coaptation structure such that the free end of the coaptation structure extends into the left heart ventricle of the patient and the coaptation structure coapts with at least one mitral valve leaflet of the patient's heart.

Preferably, the delivery of the cardiac valve repair device is via transcatheter delivery. More preferably, the delivery of the cardiac valve repair device is under fluoroscopic or ultrasound imaging guidance.

Preferably, the coaptation structure comprises a neo-leaflet.

According to another aspect of the present invention, there is a device for cardiac valve repair, the device comprising: a first upstream anchoring means adapted to anchor to a first tissue site in a patient's heart; a second upstream anchoring means adapted to engage a second tissue site in the patient's heart; and a flexible backflow barrier arranged between, and extending from the first and second upstream anchoring means, wherein the first and second tissues site are located upstream with respect to a heart valve of the patient and the backflow barrier is arranged close to the heart valve of the patient to prevent and/or minimize backflow of blood.

Preferably, the backflow barrier is substantially planar. Preferably, the backflow barrier comprises a neo-leaflet having a flexible frame. More preferably, the neo-leaflet comprises a polymer, fabric, tissue or combination thereof.

Preferably, the first upstream anchoring means is adapted to anchor at the coronary sinus of the patient's heart and the second upstream anchoring means is adapted to abut against a portion of the right arterial wall of the patient's heart.

Preferably, the first upstream anchoring means is adapted to anchor at the pulmonary vein of the patient's heart and the second upstream anchoring means is adapted to abut against a portion of the left arterial wall of the patient's heart.

According to another aspect of the present invention, there is a device for cardiac valve repair, the device comprising: an upstream anchoring means adapted to anchor to an upstream tissue site, the upstream tissue site located upstream with respect to a heart valve of a patient; and a neo-leaflet arranged to extend from the upstream anchoring means, wherein the neo-leaflet is operable to extend across the heart valve and the coaptation structure is operable to coapt with at least one heart valve leaflet of the patient's heart to prevent and/or minimize a backflow of blood.

Preferably, the device comprises a downstream anchoring means configured to extend from an end of the neo-leaflet, and wherein the downstream anchoring means is adapted to anchor at a downstream tissue site with respect to the heart valve of the patient.

Preferably, the downstream tissue site is an endocardial or pericardial tissue site of a heart ventricle of the patient.

Preferably, the upstream anchoring means is adapted to anchor at the coronary sinus of the patient's heart or optionally, the upstream anchoring means is adapted to anchor to a pulmonary vein of the patient's heart.

According to another aspect of the present invention, there is provided a device for cardiac valve repair, the device comprising: a stent adapted to anchor to at least one tissue site, the at least one tissue site located upstream with respect to a heart valve of a patient; and a neo-leaflet arranged to extend from the stent, the neo-leaflet comprising a free end distal from the stent, wherein the neo-leaflet comprises a flexible structural support frame providing flexibility to the neo-leaflet and a bioprosthetic or biocompatible material attached to the structural support frame, wherein the neo-leaflet is operable to extend across the heart valve and locate the free end downstream from the heart valve, wherein (i) the neo-leaflet is overlaid onto a surface of at least one heart valve leaflet of the patient's heart and extends beyond it to increase its length in a manner so as to serve as an extension of the at least one heart valve leaflet for coapting with at least one other heart valve leaflet of the patient's heart to prevent and/or minimize a backflow of blood, or (ii) the neo-leaflet extends across the heart valve via a commissure in between two heart valve leaflets of the patient's heart for coapting with at least one heart valve leaflet of the patient's heart to prevent and/or minimize a backflow of blood.

Preferably, the upstream tissue site is a blood vessel.

Preferably, the heart valve is a tricuspid valve, wherein the stent is adapted to:
a) anchor at a coronary sinus of the patient's heart; or
b) anchor at the inferior vena cava of the patient; or
c) anchor at the superior vena cava of the patient.

Preferably, the heart valve is a mitral valve and the stent is adapted to anchor at a pulmonary vein of the patient's heart.

Preferably, the device further comprises tethers, screws, mechanical locks, hooks, magnets, sutures, fabric, plication, crimps, staples, rivets, or adhesives adapted to connect the stent and the neo-leaflet.

Preferably, the device further comprises clamps, hooks, tines, barbs, screws or bio-adhesives extending from the free end of the neo-leaflet, wherein the clamps, hooks, tines, barbs, screws or bio-adhesives are adapted to anchor at a downstream tissue site with respect to the heart valve of the patient.

Preferably, the downstream tissue site is an endocardial or pericardial tissue site of a heart ventricle of the patient.

Preferably, the device further comprises a stabilizing structure adapted to extend across the heart valve of the patient, and wherein the stabilizing structure is configured to maintain a downstream location of the free end of the neo-leaflet wherein the stabilizing structure comprises:
a) a weighted free end; or
b) one or more stabilizing tether adapted to connect the stabilizing structure to the neo-leaflet.

Preferably, the neo-leaflet is of a petal shape.

Preferably, the neo-leaflet comprises two or more layers of bioprosthetic or biocompatible material attached to the structural support frame from two opposite sides of the structural support frame.

Preferably, the two or more layers of bioprosthetic or biocompatible material are of the same shape or sizes.

Preferably, the two or more layers of bioprosthetic or biocompatible material are of different shape and sizes.

Preferably, the neo-leaflet has a thickness of 0.1 mm to 6 mm.

According to another aspect of the present invention, there is provided a method of implanting a device for cardiac valve repair in a patient's heart, the method comprising the steps of:
a) delivering a device for cardiac valve repair to the patient's heart, the device comprising a stent and a neo-leaflet arranged to extend from the stent, the neo-leaflet comprising a free end distal from the stent, wherein the neo-leaflet comprises a flexible structural support frame providing flexibility to the neo-leaflet and a bioprosthetic or biocompatible material attached to the structural support frame;
b) anchoring the stent to at least one tissue site in the patient's heart, the at least one tissue site located upstream with respect to a heart valve of the patient's heart;
c) deploying the neo-leaflet to extend across the heart valve to locate the free end of the neo-leaflet downstream from the heart valve in a manner so as to (i) overlay the neo-leaflet onto a surface of the one heart valve leaflet of the patient's heart and extend beyond the one heart valve leaflet to increase its length to serve as an extension of the one heart valve leaflet for coapting with at least one other heart valve leaflet of the patient's heart to prevent and/or minimize a backflow of blood, or (ii) extend across the heart valve via a commissure in between two heart valve leaflets of the patient's heart for coapting with at least one heart valve leaflet of the patient's heart to prevent and/or minimize a backflow of blood.

Preferably, the method further comprises the step of testing and verifying the stability of the stent.

Preferably, the method comprises anchoring the stent at a coronary sinus of a right atrium of the patient's heart, and deploying the neo-leaflet such that the free end of the neo-leaflet extends into the right heart ventricle of the patient and the neo-leaflet coapts with at least one tricuspid valve leaflet of the patient's heart.

Preferably, the method comprises anchoring the stent at the inferior vena cava of the patient, and deploying the neo-leaflet such that the free end of the neo-leaflet extends into a right heart ventricle of the patient and the neo-leaflet coapts with at least one tricuspid valve leaflet of the patient's heart.

Preferably, the method comprises anchoring the stent at a pulmonary vein of a left atrium of the patient's heart, and deploying the neo-leaflet such that the free end of the neo-leaflet extends into the left heart ventricle of the patient and the neo-leaflet coapts with at least one mitral valve leaflet of the patient's heart.

According to another aspect of the present invention, there is provided a method of implanting a device for cardiac valve repair in a patient's heart, the method comprising the steps of:
a) delivering a device for cardiac valve repair to the patient's heart, the device comprising a stent and a single neo-leaflet arranged to extend from the stent, the neo-leaflet having a shape of one heart valve leaflet of the patient's heart or part thereof, the neo-leaflet comprising a free end distal from the stent, wherein the neo-leaflet comprises a flexible structural support frame providing flexibility to the neo-leaflet;
b) anchoring the stent to at least one tissue site in the patient's heart, the at least one tissue site located upstream with respect to a heart valve of the patient's heart;
c) deploying the neo-leaflet to extend across the heart valve to locate the free end of the neo-leaflet downstream from the heart valve by inserting the neo-leaflet across the heart valve via a commissure in between two heart valve leaflets of the patient's heart for coapting with at least one heart valve leaflet of the patient's heart to prevent and/or minimize a backflow of blood.

Preferably, the method comprises anchoring the stent at a coronary sinus of a right atrium of the patient's heart, and deploying the neo-leaflet such that the free end of the neo-leaflet extends into the right heart ventricle of the patient and the neo-leaflet extends across the heart valve via a commissure in between two tricuspid valve leaflets of the patient's heart.

BRIEF DESCRIPTION OF THE DRAWINGS

The present invention will now be described, by way of example only, with reference to the accompanying drawings, which are for illustrative purposes only and are therefore not drawn to scale, in which.

DETAILED DESCRIPTION OF THE INVENTION

Figure 1A:
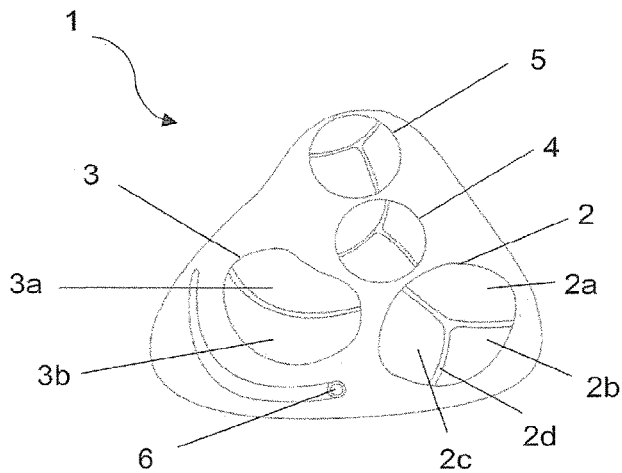
FIG. 1A is a schematic axial sectional view of a heart showing the anatomical relationship between the coronary sinus and the tricuspid valve.

Particular embodiments of the present invention will now be described with reference to the accompanying drawings. Embodiments described below in the context of the device/apparatus are analogously valid for the respective methods, and vice versa. Furthermore, it will be understood that the embodiments described below may be combined, for example, a part of one embodiment may be combined with a part of another embodiment. The terminology used herein is for the purpose of describing particular embodiments only and is not intended to limit the scope of the present invention. Other definitions for selected terms used herein may be found within the detailed description of the invention and apply throughout the description. Additionally, unless defined otherwise, all technical and scientific terms used herein have the same meanings as commonly understood by one of ordinary skill in the art to which this invention belongs. Where possible, the same reference numerals are used throughout the figures for clarity and consistency.

Throughout the specification, unless the context requires otherwise, the word "comprise" or variations such as "comprises" or "comprising, will be understood to imply the inclusion of a stated integer or group of integers but not the exclusion of any other integer or group of integers.

Furthermore, throughout the specification, unless the context requires otherwise, the word "include" or variations such as "includes" or "including" will be understood to imply the inclusion of a stated integer or group of integers but not the exclusion of any other integer or group of integers.

Throughout the specification, a "patient" includes human and animal patients. Accordingly, the cardiac valve repair device of the present invention is suitable for use in human hearts and animal hearts.

Medical terms, terminology and references used throughout the specification will have ordinary meaning in the medical field and will be understood by a skilled person in said field. Such terms, terminology and references include but are not limited to "coapt", "superior", "inferior", "posterior", "anterior", "proximal", "distal", "septal", "atrium", "ventricle" and "vena cava". Anatomical terms and references are based on the standard anatomical position of the patient, for example for humans, the anatomical position is a human standing erect, with feet facing forward, the arms at the sides, palms of the hands facing forward with thumbs pointing away from the body and fingers pointing straight down. Therefore throughout the specification and as depicted in the figures, the atrial end of a heart is considered above the ventricular end of the heart when the patient is in an anatomical position. In particular, the atrium is considered upstream from the ventricle of a heart, where blood normally flows from the atrium to the ventricle.

Throughout the specification, the terms "upstream" and "downstream" are taken with reference to a heart valve being treated/repair, and with respect to the normal flow of blood. For example, the right atrium RA is considered upstream to the right ventricle RV, since the right atrium RA is before the tricuspid valve and since blood normally flows from the right atrium RA to the right ventricle RV. Further, the right ventricle RV is considered upstream to the pulmonary artery, since the right ventricle RV is before the pulmonary valve and since blood normally flows from the right ventricle RV to the pulmonary artery. As an additional example and with reference to FIGS. 16A and 16B, the stent 811 is located at an upstream location with respect to the tricuspid valve 2 and the weighted end 816a is located at a downstream location with respect to the tricuspid valve 2.

Figure 1B:
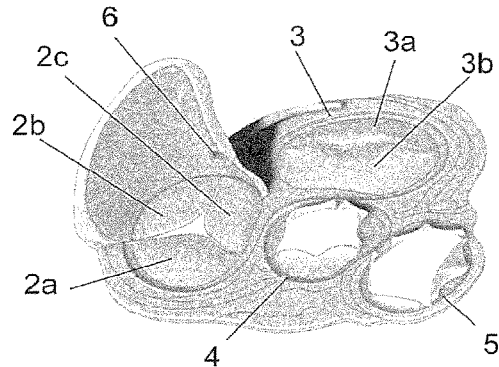
FIG. 1B is a perspective view of a 3D reconstruction of the heart section of FIG. 1A.
Figure 2:
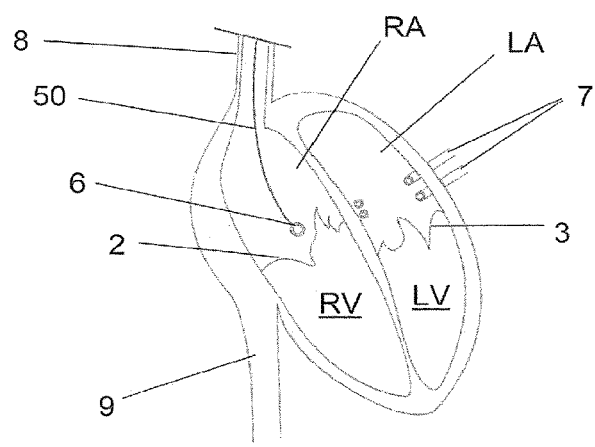
FIG. 2 is a schematic coronal view of the heart of FIG. 1 showing the anatomical relationship between the coronary sinus and the tricuspid valve. The coronary sinus is medial and superior to the tricuspid valve, generally above the posterior-septal commissure, although some variability in the position and height may exist.

FIGS. 1A, 1B and 2 provide different views of the heart and its chambers. In particular, FIG. 2 shows the anatomical relationship between the coronary sinus 6 and the tricuspid valve 2. A heart 1 comprises a right atrium RA, right ventricle RV, left atrium LA and left ventricle LV. The right atrium RA and left atrium LA are respectively separated from the right ventricle RV and left ventricle LV by the tricuspid valve 2 and mitral valve 3 (collectively known as the atrioventricular valves). The mitral valve 3 is also known as a bicuspid valve. Further, the pulmonary artery (not shown) is separated from the right ventricle LV by the pulmonary valve 5 while the aorta (not shown) is separated from the right ventricle RV by the aortic valve 4. The coronary sinus 6 is medial and superior to the tricuspid valve 2, generally above the posteroseptal commissure 2d, although some variability in the position and height may exist. The coronary sinus 6 is a collection of veins joined together to form a large vessel that collects deoxygenated blood from the heart muscle (myocardium), and delivers it to the right atrium RA.

The native atrioventricular valves comprise flexible leaflets that extend from an annulus inward towards one another, across the respective orifices. The annulus defines the boundary of the native valves. The leaflets come together or "coapt" in the flowstream to form the one-way fluid occluding surfaces. The leaflets come together at commissures, e.g. posteroseptal commissure 2d. Tricuspid valve 2 comprises anterior leaflet 2a, posterior leaflet 2b and septal leaflet 2c while mitral valve 3 comprises anterior leaflet 3a and posterior leaflet 3b. As shown, the anterior leaflet 2a, the posterior leaflet 2b and the septal leaflet 2c of the tricuspid valve 2 extend inwards from the tricuspid annulus with the posteroseptal commissure 2d being between the posterior leaflet 2b and the septal leaflet 2c, an anteroseptal commissure being between the anterior leaflet 2a and the septal leaflet 2c, and an anteropostero commissure being between the anterior leaflet 2a and the posterior leaflet 2b. The commissure is the long narrow gap bordering two adjacent valve leaflets where the two adjacent valve leaflets abut. The heart 1 also comprises chordae tendineae (not shown) which are cord-like tendons in the ventricles and which connect the papillary muscles to the tricuspid and mitral valve leaflets. The chordae tendineae prevent the eversion and prolapse of the leaflets, especially during systole, by becoming tense and pulling the leaflets, holding them in closed positions.

The right atrium RA receives deoxygenated blood from the venous system through the superior vena cava 8 and the inferior vena cava 9, while the left atrium LA receives oxygenated blood from the lungs through the pulmonary veins 7. During ventricular diastole, blood in the atria is pumped through the tricuspid valve 2 and mitral valve 3 into the ventricles, by contraction of the atria muscles and expansion (relaxation) of the ventricular muscles. During ventricular systole, the right ventricle RV contracts and pumps blood to the lungs via the pulmonary artery while the left ventricle LV contracts and pumps blood to the rest of the body via the aorta. During ventricular systole, the leaflets of the tricuspid valve 2 and mitral valve 3 close to prevent the blood from regurgitating back from the ventricles into the atria.

The present disclosure provides exemplary embodiments directed to cardiac valve repair devices and methods of implanting the same, for improving the function of a heart valve. Throughout the specification, a heart valve includes native and prosthetic/artificial heart valves. Therefore the cardiac valve repair device of the present invention is adapted to treat and/or repair native and prosthetic/artificial heart valves. Further, a heart valve includes the tricuspid valve, mitral (bicuspid) valve, pulmonary valve and the aortic valve.

Individual components of the disclosed devices may be combined unless mutually exclusive or otherwise physically impossible. Various embodiments of anchoring means, connecting means and coaptation structures are disclosed herein, and any combination of such elements may be made unless specifically excluded. For example, any of the coaptation structures may be combined with any anchoring means which includes but are not limited to stents and clamps, even if not explicitly disclosed. Likewise, the different constructions of coaptation structures may be mixed, matched and/or combined, such as combining any tissue cover with a flexible frame, even if not explicitly disclosed.

The present invention relates to a cardiac valve repair device and a method of treating heart valve regurgitation using minimally invasive approaches, where the cardiac valve repair device aims to prevent, reduce and/or minimize regurgitation of blood flow across a diseased and/or failing heart valve, or a failing prosthetic valve. The present invention also relates to a method of implanting the cardiac valve repair device. Further, the present invention relates to a new method of repairing or replacing the tricuspid valve. Additionally, the present invention is also directed to a method of delivering and producing such device.

The present invention relates to the repair or treatment of diseased heart valves or failing prosthetic heart valves using a minimally invasive or transcatheter implantable cardiac valve repair device. The present invention relates to a method of treating heart valve regurgitation using minimally invasive approaches and a device which aims to prevent, reduce and/or minimize regurgitation of blood flow across the diseased and/or failing valve or failing prosthetic valve. Native valves may lose their ability to close properly due to several reasons which include but are not limited to dilation of an annulus around the valve, ventricular dilation, or a valve leaflet being flaccid causing a prolapsing leaflet. Disease (e.g. rheumatic disease) may cause valve leaflet shrinkage, thereby leaving a gap in the valve between the valve leaflets. Prosthetic heart valves can fail from for example wear and tear, fatigue and cavitation. Regurgitation is therefore a leak backwards (i.e., from the outflow to the inflow side, or from downstream to upstream) of blood resulting from the inability of the heart valve to close properly. Heart valve regurgitation may seriously impair the function of the heart since more blood will have to be pumped through the regurgitating valve to maintain adequate circulation.

The present invention is intended to treat and repair the atrioventricular and semilunar valves, and in particular the tricuspid valve. Therefore, anatomical structures of the right atrium RA and right ventricle RV will be explained in greater detail in the specification herein, although it should be understood that the present invention may equally be used to treat or repair the mitral valve, the pulmonary valve and the aortic valve.

Cardiac Valve Repair Device

In various embodiments, the cardiac valve repair device of the present invention comprises at least one upstream anchoring means implantable above a diseased/failing valve and a coaptation structure extending into the disease valve annulus as a means to restore function of the said diseased valve. The upstream anchoring means is preferably anchored (i.e. implanted) at a tissue site located upstream with respect to the diseased/failing valve, for example in the atrial wall.

The cardiac valve repair device of the present invention is preferably a catheter-delivered device that can be percutaneously delivered for example via the venous system to the right side of the heart, although implantation of the device of the present invention may be done by for example open heart surgery. Percutaneous delivery can also be conducted via the intercostal or subxyphoid space, or an endoscopic catheter-based antegrade, retrograde, or trans-septal deployment, such methods as known in the art. The entire catheter-delivery device may then comprise of:

1. A delivery catheter;
2. An anchoring means (upstream anchoring means); and
3. A deployable valve repair (coaptation) structure which aims to restore the diseased/failing valve function.

The upstream anchoring means and the deployable coaptation structure may be implanted and deployed separately, as a single entity or some combination thereof. The deployable coaptation structure may be attachable to the anchoring means via a connecting means, which includes but is not limited to tethers. The deployable coaptation structure and the upstream anchoring means can be crimped/compressed to fit within the delivery catheter and ejected, e.g. by an obturator, from the delivery catheter to the target location, for example the upstream anchoring means being anchored to the coronary sinus.

The upstream anchoring means includes but is not limited to stents, clamps, hooks, tines, barbs, screws, and bioadhesives. Where the upstream anchoring means is for example a clamp or hook, the upstream anchoring means is capable of piercing the intended tissue site for anchorage. Such upstream anchoring means can comprise tissue (natural or artificial/engineered), metal, metal alloy, polymer or other man-made material, or a combination thereof. One or more upstream anchoring means may be used to anchor and secure the device of the present invention to one or more upstream tissue sites. Where more than one upstream anchoring means is used, the type of upstream anchoring means may be different from one another. Preferably, the upstream anchoring means is a stent. The upstream anchoring means is preferably bio-inert and/or biocompatible.

Examples of bioadhesives referred in the specification herein, include but are not limited to synthetic polymer glues such as epoxy resins, epoxy putty, ethylene-vinyl acetate, phenol formaldehyde resins, polyamides, polyester resins, polypropylene, polysulfides, polyurethane, polyvinyl acetate, polyvinyl alcohol, polyvinyl chloride, polyvinylpyrrolidone, silicones and styrene acrylic copolymer; synthetic monomer glues such as acrylnitrile, cyanoacrylate, acrylic and resorcinol glue; and solvent-type glues such as polystyrene cement/butanone and dichloromethane.

The coaptation structure includes but is not limited to balloons, flaps, leaflets and membranes. Preferably, the coaptation structure is flexible. Preferably, the coaptation structure is a neo-leaflet. In use, the coaptation structure (e.g. the neo-leaflet) coapts with at least one heart valve leaflet and/or provides a surface on which at least one heart valve leaflet can coapt against.

In various embodiments, the cardiac valve repair device may comprise a stabilizing means that maintains the location of an end of the coaptation structure in the ventricle.

In various embodiments, the device comprises one or more downstream anchoring means adapted to anchor the device to a tissue site, at a downstream location with respect to the heart valve. The downstream anchoring means may be an extension of the coaptation structure or the stabilizing means. The downstream anchoring means includes but is not limited to clamps, hooks, tines, barbs, screws and bioadhesives. Where the downstream anchoring means is for example a clamp or hook, the downstream anchoring means is capable of piercing the intended tissue site for anchoring. Such downstream anchoring means can comprise tissue (natural or artificial/engineered), metal, metal alloy, polymer or other man-made material, or a combination thereof. One or more downstream anchoring means may be used to anchor and secure the device of the present invention to one or more downstream tissue sites. Where more than one downstream anchoring means is used, the type of downstream anchoring means may be different from one another. The downstream anchoring means is preferably bio-inert and/or biocompatible.

The cardiac valve repair device may be manufactured out of a nitinol-titanium tube and manufactured by processes such as laser cutting, polishing and thermal molding in order to achieve a self-expandable implantable device comprising both an expanding stent structure and the frame of the coaptation structure. The device may also be manufactured wholly or partly from tissue (includes natural and artificial/engineered). Preferably, such tissue comprises or is capable of simulating one or more physiological functions.

Stents

Stents may be made of tissue, metal, metal alloy, polymer or other man-made material, or a combination thereof. Preferably, the stents of the present invention comprise elastic metals and/or metal alloys having shape memory, which includes but are not limited to nitinol-titanium (nitinol), Cu—Zn—Al—Ni alloys and Cu—Al—Ni alloys. Preferably the stent of the present invention comprises nitinol-titanium which allows the stent to be crimped/compressed and which allows the stent to return to its original, uncrimped/uncompressed shaped when released from for example, the delivery catheter. Nitinol-titanium can be processed to be austenitic, martensitic and/or super elastic. Martensitic and super elastic metals/metal alloys can be processed to demonstrate required compression/crimpable features.

Stents include laser cut stents or braided stents. In the manufacture of laser cut stents, a laser cuts regular cut-outs in a thin isodiametric metal/metal alloy tube. The tube is thereafter placed on a mold of the desired shape, heated to the Martensitic temperature and quenched. The treatment of the stent in this manner will form a stent that has shape memory properties and will readily revert to the memory shape at the calibrated temperature. Laser cut stents are preferably made from nitinol-titanium, but may also be made from for example stainless steel, cobalt chromium, titanium, and other functionally equivalent metals and alloys.

Braided stents are constructed using braiding techniques. A metal/metal alloy wire is wound on a braiding fixture/mandrel in an over and under braiding pattern until an isodiametric tube is formed from the wire. A coupling tube made of stainless steel or nitinol-titanium is then used to couple the loose ends of the wire. The loose ends are placed in the coupling tube and crimped. The braided stent is thereafter placed on a shaping fixture and heated to a specified temperature to set the stent to the desired shape and to develop the martensitic or super elastic properties desired.

The stent of the present invention may be made available in different sizes. Different diameter stent sizes may be provided in various embodiments of the device as the blood vessels (e.g. coronary sinus) in which the stent is to be anchored can be highly variable in size. Multiple diameters and lengths can be made available. As the stent is preferably compressible/crimpable and expandable, the diametric size of the stent can be customized and configured to the blood vessel in which it anchors, for example a balloon catheter can be made to radially expand the stent such that the stents abuts and lodges into the tissue of a blood vessel so as to improve the anchorage and stability of the stent at the tissue site/blood vessel.

The stent of the present invention may be an expandable stent, and the expandable stent may be self-expanding or balloon expandable. Preferably, the stent is flexible.

The stent may comprise tines and barbs arranged along an outer surface that latch onto tissue, to improve anchorage and stability of the stent.

Coaptation Structure

Various coaptation structures may be used in the cardiac valve repair device of the present invention. The coaptation structure includes but is not limited to balloons, flaps, leaflets and membranes. Preferably, the coaptation structure is flexible. Preferably, the coaptation structure is a neo-leaflet. The coaptation structure is shaped to extend across a patient's heart valve and position/locate one of its ends downstream with respect to the heart valve, for example, the coaptation structure is arranged to extend into a right heart ventricle across a tricuspid valve. The coaptation structure preferably extends into the heart ventricle substantially via the centre of the heart valve annulus, or via the commissures (i.e. between adjacent valve leaflets), or on and/or laid over a surface of a heart valve leaflet, etc. In various embodiments, the coaptation structure or part thereof extends into the heart ventricle via the valve commissures, i.e. between adjacent valve leaflets. For example, the neo-leaflet is arranged to extend into the heart ventricle substantially via the centre of the heart valve annulus, or via the commissures (i.e. between adjacent valve leaflets), or on and/or laid over a surface of a heart valve leaflet, etc.

The coaptation structure is constructed so as to provide sufficient structural integrity to withstand the intracardiac forces without collapsing. Choice of, shape and size of the coaptation structure depends on a physician's preference, which in turn depends on for example the patient's heart anatomy and condition. Importantly, the coaptation structure allows blood to flow from the atrium into the ventricle, without or with minimal regurgitation of flow, thereby restoring valve function.

The coaptation structure includes but is not limited to balloons, flaps, leaflets and membranes. Throughout the specification where the coaptation structure is a flap or leaflet or membrane, the coaptation structure will be referred to as a "neo-leaflet", to differentiate the coaptation structure of the present invention, from the native valve leaflets and/or prosthetic valve leaflets that the cardiac valve repair device is intended to treat, repair and/or replace.

Preferably, the coaptation structure is flexible.

The coaptation structure can be made from tissue (or bioprosthetic material), biocompatible and/or bio-inert materials or combinations thereof. Tissue (or bioprosthetic material) includes but is not limited to biological animal tissue which may be chemically stabilized, for example bovine (cow) pericardium, ovine (sheep) pericardium, porcine (pig) pericardium or equine (horse) pericardium, and engineered tissue.

Biocompatible and/or bio-inert materials include but are not limited to metals, fabrics and polymers. Biocompatible polymers include but are not limited to polyurethane, polyethylene terephthalate (PET), polytetrafluoroethylene (PTFE), polyetheretherketone (PEEK), polystyrene-b-polyisobutylene-b-polystyrene (SIBS), polyester, polycarbonate urethane, polycarbonate silicone, polyether urethane, segmented polyether urethane, silicone polyether urethane, silicone, polycarbonate urethane, ultrahigh molecular weight polyethylene, polyolefin, elastomers, nylon, polyethyleneglycols, polyethersulphones, polysulphones, polyvinylpyrrolidones, polyvinylchlorides, other fluoropolymers, silicone polyesters, siloxane polymers and/or oligomers, polylactones and block co-polymers.

The coaptation structure or part thereof may be treated with additives, for example, immunosuppressants and anti-coagulants (such as heparin).

In various embodiments, the coaptation structure comprises a structural support frame which maintains the shape, size and flexibility of the coaptation structure. The structural support frame may be made from tissue (natural or artificial/engineered) metals, metal alloys, polymers, or a combination thereof. Preferably the structural support frame is made from elastic metals and/or metal alloys having shape memory, which includes but are not limited to nitinol titanium (nitinol), Cu—Zn—Al—Ni alloys and Cu—Al—Ni alloys. More preferably, the structural support frame is made from nitinol-titanium.

In various embodiments, the coaptation structure is a balloon, where the structural support frame (for example comprising structural ribs) which provides the shape of the balloon, can be covered by bioprosthetic tissues and/or biocompatible synthetic materials. The balloon may be in the form of a rounded structure, having a tubular, ovoid or near-spherical shape that can act as a supporting occluding element, which can be centrally located within the heart valve being repaired, to facilitate coaptation of the valve leaflets around the balloon to prevent flow regurgitation. In the particular cases of the mitral and tricuspid valves, the failing leaflets may not be coapting thereby leaving a gap in the valve that causes the regurgitation of flow from the ventricle into the atrium during the systolic phase. The balloon as an occluding coaptation structure, acts as a support that restores the coaptation of the failing or prolapsing leaflet, thereby preventing flow from regurgitating from the ventricle back into the right atrium. The balloon provides a surface for coaptation of at least one heart valve leaflet.

The balloon can have various radial shape profiles and such shape profiles may vary along the length of the balloon, for example one end portion of the balloon may be circular while the other end is triangular. The balloon can have various sizes (i.e. radial diameter) and lengths. The size and length of the balloon can depend on for example, the size of the valve annulus and the length of the heart valve leaflets.

The balloon is preferably shaped and sized to provide an exterior surface for the valve leaflets to coapt against. Preferably, the exterior surface of the balloon is continuous.

In various embodiments, the balloon is self-expandable upon delivery or is capable of being inflated in a similar fashion as a balloon catheter, e.g. via an external access port.

In various embodiments, the coaptation structure is a neo-leaflet, where a wire (or a plurality of wires) is shaped to form the structural support frame for the neo-leaflet, and the bioprosthetic and/or biocompatible material covers the frame. Layers/sheets of material (e.g. bioprosthetic and/or biocompatible material) may be attached to the structural support frame from two opposite sides of the structural support frame to cover the structural support frame. The structural support frame may be in the form of, including but not limited to, a midrib structure or a skeleton structure or a fishbone structure or a sternum structure or a central support structure or a boundary frame structure. The structural support frame provides flexibility to the neo-leaflet, such that the neo-leaflet is capable of functioning (or movable) in a substantially similar manner as natural heart valve leaflets. The neo-leaflet is capable of acting as an extension of a failing valve leaflet to restore valve coaptation and prevent leaflet prolapse. In various embodiments, the neo-leaflet may be formed from an animal tissue having an inherent structural frame such that the neo-leaflet does not require a separate structural support frame formed from a metal, metal alloy, polymer or a combination thereof.

The neo-leaflet can have various shapes and sizes, for example the shape of a tricuspid valve leaflet or part thereof (i.e. the neo-leaflet has a shape of the heart valve leaflet or part thereof). Accordingly, the neo-leaflet may be of a petal/paddle-shaped. Similarly, when the neo-leaflet is to be used in a mitral valve, the neo-leaflet can have the shape of a mitral valve leaflet or part therof (i.e. the neo-leaflet has a shape of the heart valve leaflet or part thereof). The shape and size of the neo-leaflet depends on for example the length of the heart valve leaflets. The neo-leaflet can have different number of layers/sheets of material being stacked together to form the neo-leaflet (for example see FIG. 20A to 22B). For example, the neo-leaflet may have two or three or four or more layers/sheets overlaid onto each other (or placed over and upon another). At least one layer/sheet of material may be attached to the structural support frame from a first side of the structural support frame and at least one other layer/sheet of material may be attached to the structural support frame from a second side of the structural support frame, whereby the first side and the second side are opposite sides of the structural support frame. Accordingly, due to different number of layers/sheets of material, the neo-leaflet can have different thickness. For example, the neo-leaflet may have a thickness of 0.1 mm to 6 mm. The neo-leaflet can have uniform thickness along its length. For example, when each of the layers/sheets has the same shape and sizes, the neo-leaflet may have uniform thickness (see for example FIG. 21A to 22B). Further, the neo-leaflet can have different (or uneven or non-uniform) thickness along its length. For example, when each of the layers/sheets has different shape and sizes, the neo-leaflet may have different thickness (see for example FIGS. 20A and 20B). The length of the neo-leaflet may be measured from an end of the neo-leaflet directed towards the upstream anchoring means (e.g. stent) to an end directed away or farthest from the upstream anchoring means (e.g. stent). The neo-leaflet may have a surface area between 225 mm$^2$ to 2025 mm$^2$. The neo-leaflet may a width/length between 15 mm to 45 mm. Accordingly, the neo-leaflet may have a length-to-thickness ratio between 2.5 to 450, or a surface-area-to-thickness ratio between 37.5 to 20250.

In various embodiments, the neo-leaflet or part thereof is expandable.

In various embodiments, the coaptation structure or part thereof may be inserted via a commissure in between two heart valve leaflets to the ventricular side of the valve where once deployed, it prevents reflux of flow by acting as a one way valve together with the patient's heart valve leaflets.

In various embodiments, the coaptation structure may be inserted in the commissure in between two valve leaflets in order to act as a membrane wall structure on which the leaflets can coapt, thereby preventing their prolapse and flow regurgitation. In such embodiments, the coaptation structure is a membrane or a neo-leaflet. Accordingly, the membrane or neo-leaflet may be inserted along (or slotted through) the commissure. For example, the membrane or neo-leaflet may be inserted edge first into the commissure so as to lie between the two valve leaflets. When the membrane or the neo-leaflet is at the commissure, the membrane or the neo-leaflet may serve as a septum or a "curtain" between the two heart valve leaflets.

Connecting Means

In various embodiments, the deployable coaptation structure and the upstream anchoring means are a single unitary structure. In other various embodiments, the deployable coaptation structure and upstream anchoring means are separate structures, and the coaptation structure is attachable and securable to the upstream anchoring means by one or more connecting means. In various embodiments, the connecting means is adapted to arrange the coaptation structure at an intended location with respect to the valve/valve leaflets, e.g. centre of a heart valve (or valve annulus), in a commissure between two heart valve leaflets, on and/or laid over a surface of a heart valve leaflet, etc.

The connecting means may be integral with the coaptation structure or the upstream anchoring means. The connecting means includes but is not limited to tethers, screws, mechanical locks, hooks, magnets, sutures (regardless of calibre or material), fabric, plication, crimps, staples, rivets, adhesives and any other device, component or method typically used to assemble various elements in an implantable device. The connecting means is preferably biocompatible and/or bio-inert.

It should be conceivable that there may be different sizes and shapes of the components of the cardiac valve repair device of the present invention, available to account for the distance between the tissue site at which the upstream anchoring means anchors and the heart valve being treated/repaired, and the size of the heart valve being treated/repaired. Therefore in various embodiments, the connecting means is capable of varying the distance between the upstream anchoring means and the coaptation structure, for example by varying its length. Therefore, the length of the connecting means will depend on the application of the present invention and requirements of the patient and/or the physician. Preferably, the connecting means is a tether (which includes rods and wires). Accordingly, the connecting means (e.g. the tether) extends between or interconnects the upstream anchoring means (e.g. a stent) and the coaptation structure (e.g. a neo-leaflet). A physician can measure the distance between the upstream anchoring means and the coaptation structure before determining the optimal length of the connecting means.

Tethers may be made from biocompatible and/or bio-inert materials which include but are not limited to polymers (such as PTFE and polypropylene), metals, metal alloys (such as nitinol-titanium) and tissue (natural or artificial/engineered). Tethers may be formed from a single wire or comprise more than one wire braided together. Tethers may be inelastic or elastic. Tethers may be flexible, which can contribute to the flexibility of the coaptation structure of the present invention.

Stabilizing Means

In various embodiments, the cardiac valve repair device comprises a stabilizing means that maintains an end of the coaptation structure at a downstream location with respect to a heart valve. The stabilizing means may be an extension of the coaptation structure, the upstream anchoring means or the connecting means. The stabilizing means extends substantially to a downstream location across the heart valve, e.g. into a heart ventricle and is connected via for example tethers, to an end of the coaptation structure to maintain its downstream location. Such tethers (stabilizing tethers) function in the similar manner like natural chordae tendinae which prevent the prolapse retraction of the coaptation structure, especially during systole, by becoming tense and pulling on the coaptation structure. In various embodiments where the coaptation structure is a neo-leaflet, such tethers prevent the eversion and prolapse of the neo-leaflet, especially during systole, by becoming tense and pulling on the neo-leaflet.

The stabilizing means may be made from metals, metal alloys, polymers, tissue (natural or artificial/engineered) or a combination thereof. The stabilizing means is preferably flexible and made from a shape memory material. Preferably, the stabilizing means is made from a material having a sufficiently high elasticity modulus that allows the stabilizing means to maintain its shape during operation. The stabilizing means may be made from metal, metal alloy, polymer or other man-made material, or a combination thereof. Preferably the stabilizing means comprises metals and/or metal alloys having shape memory, which includes but are not limited to nitinol titanium (nitinol), Cu—Zn—Al—Ni alloys and Cu—Al—Ni alloys. Preferably the stabilizing means is made from nitinol-titanium.

In various embodiments, the stabilizing means comprises a weighted end.

In various embodiments, the stabilizing means comprises one or more downstream anchoring means adapted to anchor the device to a tissue site, at a downstream location with respect to the heart valve, e.g. ventricular side of the valve. The stabilizing means stabilize the coaptation structure across the heart valve which may advantageously prevent the cardiac valve repair device from migrating over the cardiac cycle and over time.

The downstream anchoring means includes but is not limited to clamps, hooks, tines, barbs, screws and bio-adhesives. Where the downstream anchoring means is for example a clamp or hook, the downstream anchoring means is capable of piercing the intended tissue site for anchoring. Such tissue sites include but are not limited to endocardial and pericardial tissue sites.

The downstream anchoring means may be integral with the stabilizing means and can comprise tissue (natural or artificial/engineered), metals, metal alloys, polymers or other man-made materials, or a combination thereof. One or more downstream anchoring means may be used to anchor and secure the device of the present invention to one or more downstream tissue sites. Where more than one downstream anchoring means is used, the type of downstream anchoring means may be different from one another. The downstream anchoring means is preferably bio-inert and/or biocompatible.

Method of Delivery, Deployment and Implantation of the Cardiac Valve Repair Device The present invention includes methods of delivery, deployment and implantation of the cardiac valve repair device of the present invention. The delivery of the cardiac valve repair device of the present invention may be a single or multi-step process. A method of delivering such device may comprise the use of a delivery catheter inserted through minimally invasive access and advanced by fluoroscopic and ultrasound (Echo) guidance. Echocardiographic and/or CT (computerized tomography) and/or MRI (magnetic resonance imaging) evaluation may be required pre-operatively to determine the 3D-relationship between the tissue site (e.g. coronary sinus) and the heart valve (e.g. tricuspid valve). It is expected that patients with a pacing lead in the coronary sinus or in the right ventricle may be unsuitable for this therapy. The methods of the present invention may also not be performed in patients with infective endocarditis.

In various particular embodiments, the method of delivery may include using access from the femoral vein, internal jugular or subclavian vein, to access the coronary sinus. A marker catheter may be used to size the coronary sinus. This can be performed by an imaging modality such as ultrasound echocardiography, Transesophageal echocardiography, intravascular ultrasound or by fluoroscopy with injection of contrast. The marker catheter is then exchanged for the delivery system, using a guidewire.

With the delivery system in place, the upstream anchoring means (e.g. stent) is deployed at the orifice of the coronary sinus and stability is verified. Stability testing may include tug testing. The deployable coaptation structure (e.g. neo-leaflet) is then deployed, for example in the right atrium RA and guided into the right ventricle RV. This may be performed with a specialized catheter or part of the delivery catheter.

Alternatively, the coaptation structure (e.g. neo-leaflet) is positioned directly in the right ventricle RV before full deployment, again by the delivery catheter. Once the coaptation structure is deployed, echocardiographic and fluoroscopic assessment can be performed to confirm device positioning and adequate reduction of tricuspid regurgitation. The upstream anchoring means (e.g. stent) of the device is then deployed to hold the coaptation structure in place as a secondary step.

Deployment of the coaptation structure may depend on its actual shape and size. It may be unfurled, untwisted, unsheathed, or unrolled. It may be deployed in a single or multi-step process.

In various embodiments, a delivery device, e.g. a delivery catheter carries the cardiac valve repair device of the present invention, where the device comprises the upstream anchoring means (e.g. a stent) and the coaptation structure (e.g. a neo-leaflet) as a single unitary structure. The coaptation structure may be deployed first followed by the upstream anchoring means or vice versa. For example where the cardiac valve repair device is adapted to treat/repair a tricuspid valve, the upstream anchoring means is a stent operable to anchor at the inferior vena cava and the coaptation structure comprises a neo-leaflet, the neo-leaflet can be deployed in the right ventricle and then withdrawn partially into the right atrium, and thereafter, the rest of the cardiac valve repair device is pulled back into the inferior vena cava where the stent is anchored to the inferior vena cava. Hence, the sequence of delivery of the cardiac valve repair device may be as follows:

delivery system (delivery catheter comprising the cardiac valve repair device) is navigated from inferior vena cava to right atrium into right ventricle across tricuspid valve;

the distal end of the neo-leaflet as the coaptation structure is released into the right ventricle and unfurled as the delivery catheter is pulled back into the right atrium where the proximal part of the neo-leaflet will sit/locate; and the catheter is pulled back further into the inferior vena cava where the stent as the upstream anchoring means is deployed with the neo-leaflet attached to the stent— the neo-leaflet may be integral with the stent, or be attached to the stent via a connecting means (e.g. bioadhesives, stitches, hooks and tethers).

In various embodiments, the delivery, deployment and implantation of the cardiac valve repair device comprises a multi-step process where for example, the upstream anchoring means, e.g. the stent is first delivered and anchored to the coronary sinus or inferior vena cava before the coaptation structure, e.g. neo-leaflet is delivered and secured to the upstream anchoring means, and deployed across the tricuspid valve. The coaptation structure (e.g. neo-leaflet) may be deployed across the tricuspid valve via a centre of the tricuspid valve (or the tricuspid annulus), a commissure between two tricuspid valve leaflets, on and/or laid over a surface of a tricuspid valve leaflet, etc.

In one aspect, the present invention relates to a method of treating or repairing a heart valve by a minimally invasive approach, comprising the steps of advancing an upstream anchoring means (e.g. stent) to an anchoring location (preferably a vessel ostium) of a heart chamber, in the vicinity of the heart valve and deploying the upstream anchoring means at the location, and deploying the deployable coaptation structure (e.g. a neo-leaflet) and ensuring the function of the coaptation structure to restore valve function. The procedure may include advancing an additional catheter to pass the distal part of the coaptation structure across the valve. It is understood that these steps may be performed in a different reverse order.

In a particular embodiment of a tricuspid valve repair, the invention relates to a method of delivering and implanting a cardiac valve repair device of the present invention, the method comprising the steps of catheterizing the coronary sinus and delivering the upstream anchoring means (e.g. stent), and deploying a coaptation structure (e.g. neo-leaflet) across the tricuspid valve to restore valve function. It is understood that each of the steps described above may occur in a different order.

In a particular embodiment of a mitral valve repair, the invention relates to a method of delivering and implanting a cardiac valve repair device of the present invention, the method comprising the steps of catheterizing one of the pulmonary veins and delivering the upstream anchoring means (e.g. stent), and deploying a coaptation structure (e.g. a neo-leaflet) across the mitral valve to restore valve function. It is understood that each of the steps described above may occur in a different order.

In both tricuspid and mitral valve repairs, the delivery of the cardiac valve repair device can be advanced in the right or left atrium, via the femoral vein, internal jugular or subclavian vein and a transeptal puncture.

It is understood that while particular cases of tricuspid and mitral valve repair are described, a device according to the principles of the present invention may be used to correct valve regurgitation in the aortic valve or in the pulmonary valve as well.

In various embodiments, each component of the cardiac repair are retrievable and removable from a patient via the delivery catheter system.

Exemplary Embodiments of the Present Invention

Cardiac Valve Repair Device

FIGS. 1 and 2 are schematic views of the heart 1 showing the anatomical relationship between the different valve positions in an axial view (FIGS. 1A and 1B) and a coronal view (FIG. 2). The position of the ostia of coronary sinus 6 and pulmonary veins 7 can be observed above the tricuspid valve 2 and the mitral valve 3 respectively. In FIG. 2, a guidewire 50 is shown advanced into the coronary sinus 6 from the superior vena cava 8. During heart minimally invasive procedures, a guidewire 50 is often used during the heart catheterization to obtain a guide path from the access point to a desired location and to advance a guiding catheter sheath and other catheters to that particular desired location. Such a wire or guide catheter may be used here for advancing and delivering the cardiac valve repair device of the present invention into the coronary sinus 6.

Figure 3:
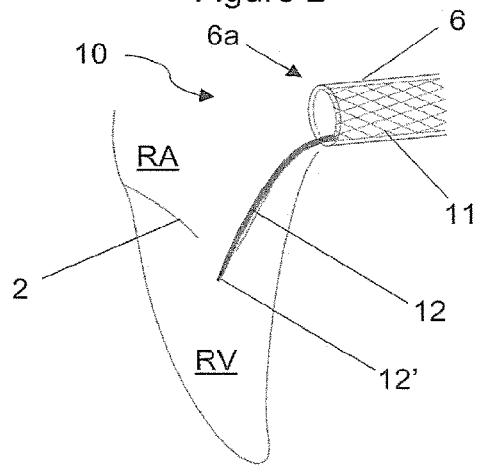
FIG. 3 is a schematic coronal section of the right heart atrium RA and ventricle RV with the cardiac valve repair device according to an embodiment of the present invention. The device 10 comprises a stent 11 anchored in the coronary sinus 6 and a deployable coaptation structure 12 extending into the right ventricle RV, functioning as a one-way valve repair.

FIGS. 3 to 5, 14 and 15 provide an embodiment of a cardiac valve repair device 10 of the present invention. FIG. 3 shows a schematic magnified view of the anatomy shown in FIG. 2, showing the right heart ventricle RV and tricuspid valve 2 with a cardiac valve repair device 10 according to an embodiment of the present invention. The cardiac valve repair device 10 comprises a stent 11 as an upstream anchoring means and a neo-leaflet 12 as a deployable coaptation structure. The neo-leaflet 12 extends from the stent 11 at a border 11a located at one end of the stent 11. Preferably, the neo-leaflet 12 extends from an inferior border 11a of the stent 11 such that when the device 10 is implanted in the correct orientation in the patient's heart, the neo-leaflet 12 is positioned close to the heart valve for said neo-leaflet 12 to function as described herein. The inferior border 11a will be understood to be a lower portion of an end of the stent 11 when the stent 11 is implanted in a correct orientation in for example the coronary sinus 6 (FIG. 5C). In various embodiments, the inferior border 11a is the lowest tip of an end of the stent 11 when the stent 11 is implanted in a correct orientation. It will be appreciated that depending on the application and requirements, the neo-leaflet 12 (as the coaptation structure) is attachable to one or more portions of the stent 11 (as the upstream anchoring means) which includes but is not limited to an inner luminal surface, an outer luminal surface, and anywhere along the length of the stent 11, for example the end and medial portions of the stent 11. Preferably, the neo-leaflet 12 is attachable (e.g. via stitching, hooks and/or screws) to an inner border, surface, lumen and/or portion of the stent 11.

Figure 5A:
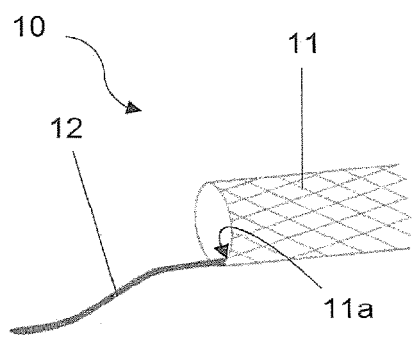
FIG. 5A is a schematic side profile drawing of a cardiac valve repair device according an embodiment of the present invention, with a stent 11 and a deployable coaptation structure 12 extending from the inferior border 11a of the stent 11.
Figure 14:
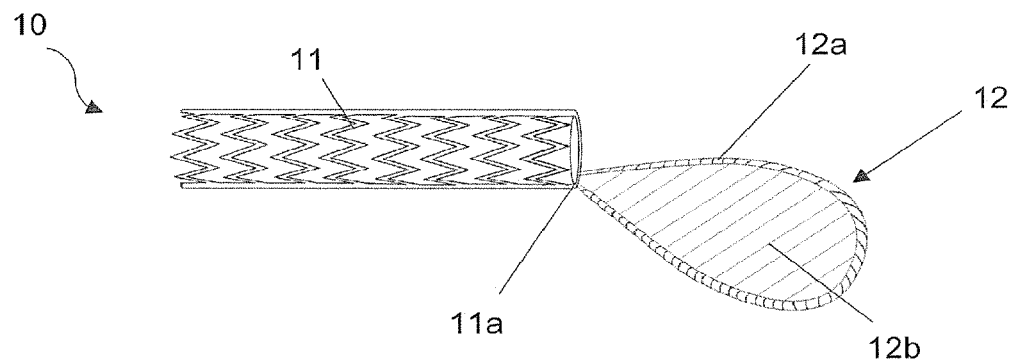
FIG. 14 is a schematic perspective view of a cardiac valve repair device according to the embodiment of FIGS. 5A to 5C.

The stent 11 and neo-leaflet 12 form a unitary structure, where the material of the stent 11 is used to form a part of the neo-leaflet 12. With reference to FIG. 14, the stent 11 is made from a metal alloy, preferably nitinol-titanium, comprising a portion which extends to form a structural support frame 12a that forms the leaflet/flap shape of the neo-leaflet 12. The structural support frame provides the neo-leaflet 12 with a curved side profile as shown in FIG. 5A. Bioprosthetic material 12b is attached, e.g. via stitching, hooks and/or screws to the structural support frame 12a to complete the neo-leaflet 12. The structural support frame 12a holds the neo-leaflet 12 in position during operation of the device 10 and provides the required rigidity to the neo-leaflet 12 to prevent prolapse of the distal section of the neo-leaflet 12. The structural support frame 12a also provides the required flexibility for the neo-leaflet 12 to function in a substantially similar manner as a normal native valve leaflet for coaptation with the heart valve leaflets during operation. In various embodiments, the neo-leaflet 12 comprises a shape that substantially corresponds to the medial portion of the septal leaflet 2c (i.e. the neo-leaflet 12 has a shape of the heart valve leaflet or part thereof).

In various embodiments, the stent 11 and neo-leaflet 12 are separate components, and the neo-leaflet 12 is attachable to the stent 11 at the border 11a via means and methods disclosed herein, for example via stitching, bioadhesives, hooks and/or screws.

Figure 4:
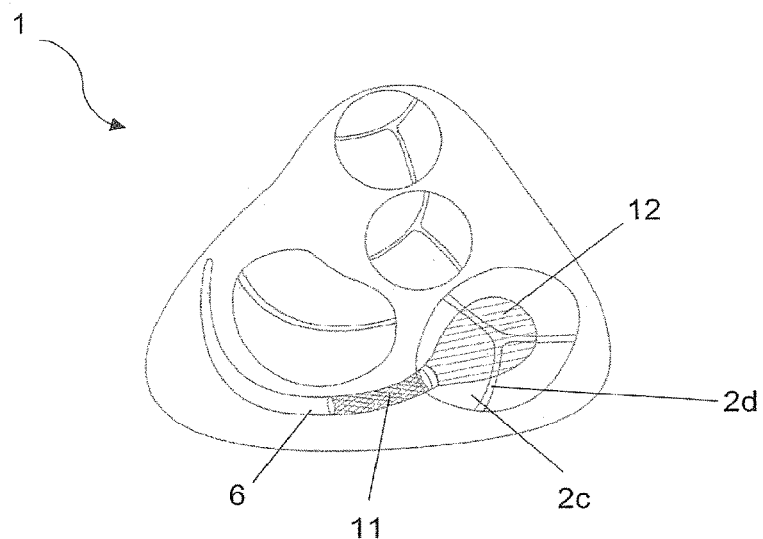
FIG. 4 is a schematic axial sectional view of the cardiac valve repair device according to an embodiment of the present invention as shown in FIG. 3, with the deployable coaptation structure 12 shaped as a neo-leaflet extending into the right ventricle.
Figure 15:
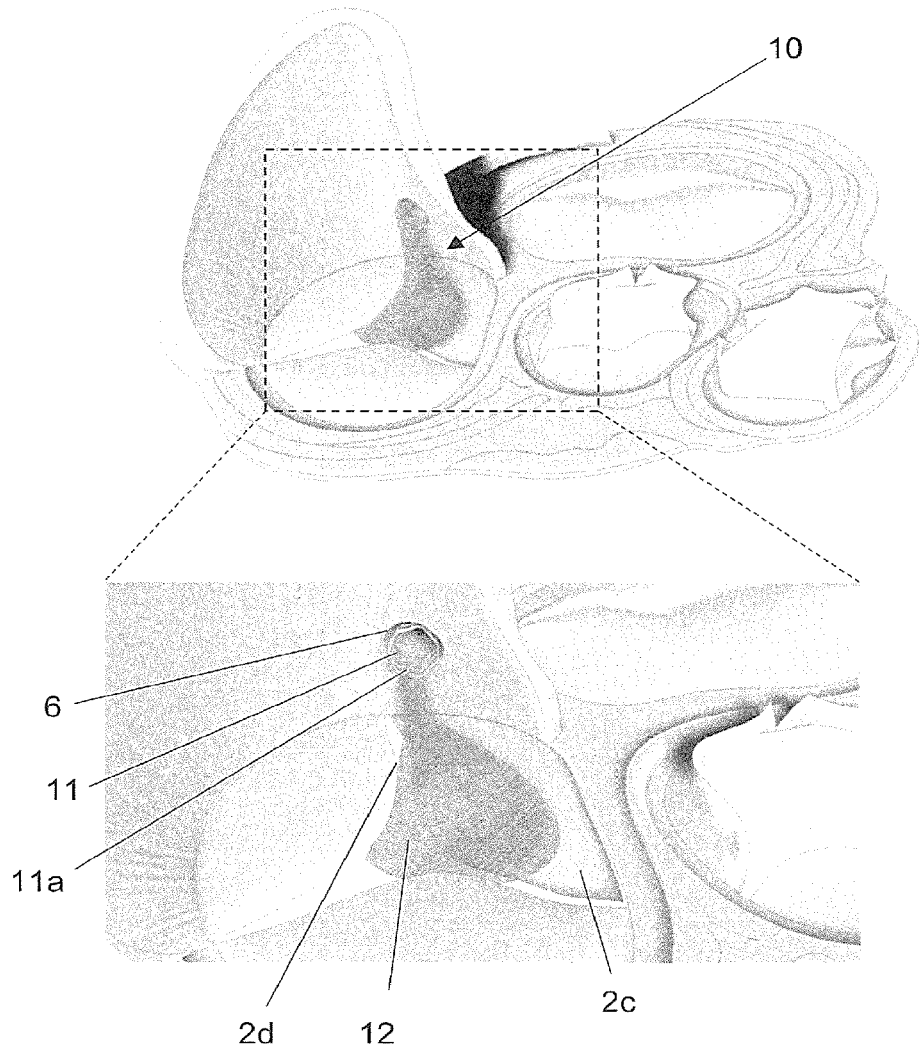
FIG. 15 is a perspective and enlarged view of a 3D reconstruction of a cardiac valve repair device according the embodiment of FIGS. 5A to 5C, implanted in the right atrium of a heart, where the stent 11 is anchored at the coronary sinus 6, and the coaptation structure 12 extends into the right ventricle via the tricuspid valve.

The stent 11 is implantable in a coronary sinus 6, with the border 11a preferably located substantially at the ostium 6a of the coronary sinus 6. The stent 11 can be crimped/compressed and catheter delivered to the coronary sinus 6 before being expanded and implanted in the coronary sinus 6. The stability of the stent 11 in the coronary sinus 6 can be tested via tug testing. The neo-leaflet 12 is deployed and extends across the tricuspid valve 2 and into the right ventricle RV, preferably via a location (first location) substantially at the centre of the tricuspid valve 2. In particular, the neo-leaflet 12 extends across the tricuspid valve 2 to locate a free end 12' of the neo-leaflet 12 downstream from the tricuspid valve 2, in the right ventricle RV. The free end 12' is preferably located downstream from the tricuspid valve 2 at all times when in operation, i.e. during both systolic and diastolic phases. The free end 12' is distal from the stent 11. The free end 12' is allowed to move substantially unrestricted during the cardiac cycle, but remains downstream from the heart valve. In various embodiments, the free end 12' is not anchored to a tissue site. When a heart valve is non-functional and regurgitation is present, the leaflets of the valve typically do not coapt together completely and instead of the valve closing, flow is regurgitating through an area of the valve into the atrium, affecting the heart pumping mechanism. The neo-leaflet 12 acts as a mechanism to restore the tricuspid valve 2 function, which is to close during the ventricular systolic phase in order for the blood in the right ventricle RV to be ejected through the pulmonary valve 5. As shown in FIGS. 3, 4 and 15, the neo-leaflet 12 extends (or is overlaid) onto at least one of the native valve leaflets, extending beyond it to increase the length available for coaptation. Therefore in operation, the neo-leaflet 12 is an extension of and functions (or moves) like the septal leaflet 2c, which coapts against the anterior leaflet 2a and posterior leaflet 2b during ventricular systole, thereby preventing, reducing and/or minimizing backflow of blood (i.e. regurgitation). Preferably, the neo-leaflet 12 extends (or is overlaid) substantially onto the septal leaflet 2c. In various embodiments, portions of the neo-leaflet 12 extend into the right ventricle RV at other locations, for example via a commissure in between valve leaflets, for example commissure 2d, between posterior leaflet 2b and septal leaflet 2c. For example, peripheral edges of the neo-leaflet 12 may extend beyond a corresponding edge of the valve leaflet so as to extend into the commissure 2d between valve leaflets 2b, 2c.

The cardiac valve repair device 10 is advantageous because it can be implanted efficiently via minimally invasive means known in the art. The stent 11 can be easily anchored to the upstream tissue site which is a blood vessel, and the neo-leaflet 12 can be easily deployed to extend across the failing valve to expeditiously restore valve functions by coapting with the other valve leaflets.

Figure 6:
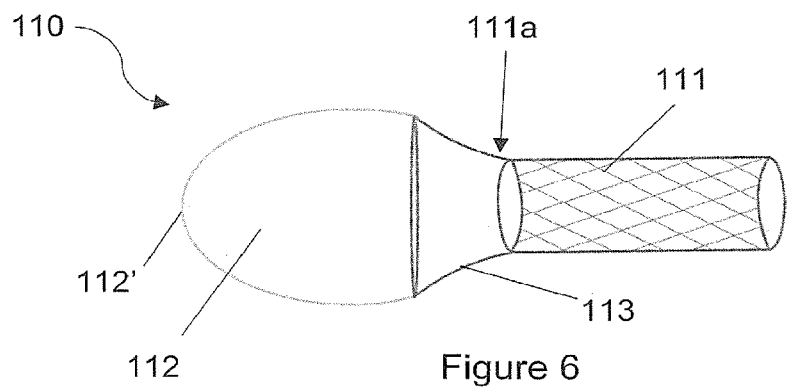
FIG. 6 is a schematic view of a cardiac valve repair device according to an embodiment of the present invention, with a deployable coaptation structure 112 connected to the stent 111 by tethers 113.

FIG. 6 provides another embodiment of a cardiac valve repair device 110 comprising a stent 111 and a neo-leaflet 112 which is attached to the stent 111 via connecting tethers (connecting wires) 113. The neo-leaflet 112 is a petal/paddle-shaped flap. During operation of the device 110, the tethers 113 extend the deployed neo-leaflet 112 towards an intended location (e.g. the centre between valve leaflets, or a commissure between two valve leaflets, or on and/or laid over a surface of a valve leaflet, etc.) in the heart valve, arrange and substantially maintain the orientation and position of the neo-leaflet 112 at the intended location(s). The positioning of the neo-leaflet 112 at the intended location(s) optimizes the efficiency of the device 110 in the repair/treatment of the heart valve by ensuring maximal coaptation between the valve leaflets and the neo-leaflet 112. The tethers 113 are therefore preferably made from a shape memory metal alloy, e.g. nitinol-titanium, such that they can effectively maintain the position of the neo-leaflet 112 at the intended location(s).

In FIG. 6, the stent 111, neo-leaflet 112 and tethers 113 are a single unitary structure, where the tethers 113 extend from the stent 111 to the neo-leaflet 112 and forms the shape and structure of the neo-leaflet 112. It will however be appreciated that in other embodiments, the stent 111 and the neo-leaflet 112 are separate components, which are attachable to one another via the tethers 113. The attachment point may be at either or both ends of the tethers 113 (i.e. at the border 111a and/or the neo-leaflet 112), or at a medial portion of the tethers 113.

The tethers 113 are preferably flexible, thereby providing additional flexibility to the cardiac valve repair device 110 during operation. The length of the tethers 113 depends on the application of the present invention and the requirements of the patient and/or physician. For example, the tethers 113 can comprise a length that substantially corresponds to the distance of ostium 6a of the coronary sinus 6 to the tricuspid valve 2, of a patient. To avoid substantial variations in the length of the tethers 113 during operation, the tethers 113 are preferably non-elastic.

Figure 7:
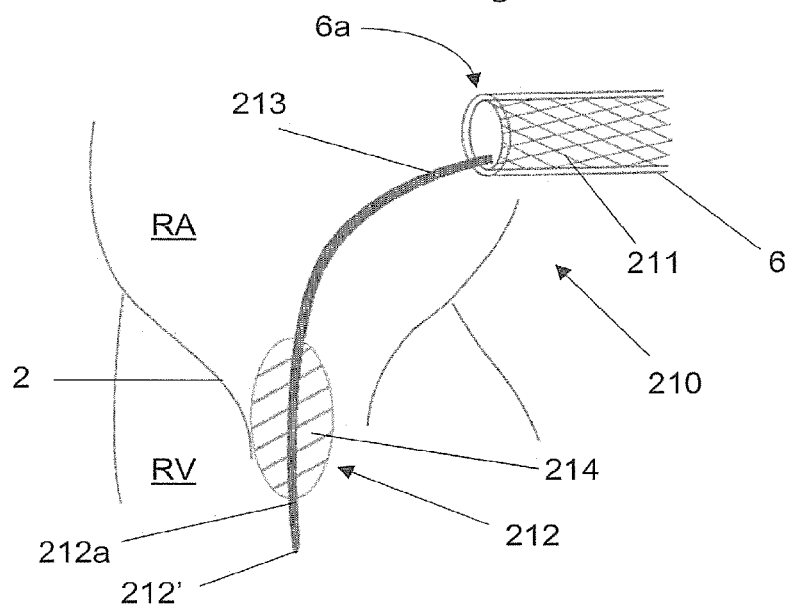
FIG. 7 is a schematic view of a cardiac valve repair device according to an embodiment of the present invention, with a stent 211 implanted in a coronary sinus 6 above the valve 2 and a coaptation structure 212 with an expanded portion 214 located in the middle of the valve 2 providing a support for the coaptation of a heart valve leaflet.

FIG. 7 provides another embodiment of a cardiac valve repair device 210 comprising a stent 211 implanted into the coronary sinus 6, tether 213 and a coaptation structure 212 extending across the tricuspid valve 2 and into the right ventricle RV via a central location between tricuspid valve leaflets. During operation (i.e. during systolic and diastolic phase), the coaptation structure 212 extends across the tricuspid valve 2 to locate a free end 212' of the coaptation structure 212 downstream from the tricuspid valve 2, in the right ventricle RV. The coaptation structure 212 is a balloon 212 comprising a structure support frame 212a and an expandable portion 214 having a surface for coaptation with at least one valve leaflet so as to prevent, reduce and/or minimize a backflow of blood, when in operation.

The expandable portion 214 can be self-expandable or can be expanded via a balloon catheter. When in operation, the expandable portion 214 is positioned within the valve 2 via tethers 213 such that the expandable portion 214 or a portion thereof, provides a support for coaptation of valve leaflets. Therefore the expandable portion 214 comprises a length that sufficiently extends into the ventricle between valve leaflets, thereby providing a support for coaptation of the valve leaflets. Such length can depend on for example, the distance between the upstream tissue anchorage site and the valve, and/or the length of the heart valve leaflet. It will be appreciated that the length of heart valve leaflets are often mismatched, and therefore the different lengths of the heart valve leaflets have to be taken into consideration when determining the length of the expandable portion 214 (or a neo-leaflet). Accordingly, the expandable portion 214 can extend the entire length (i.e. to the end) of the structural support frame 212a or a part thereof.

In other embodiments, the coaptation structure 212 is an expandable neo-leaflet 212, where a portion of the neo-leaflet 212, e.g. the portion comprising the bioprosthetic tissue, is expandable.

Figure 5B:
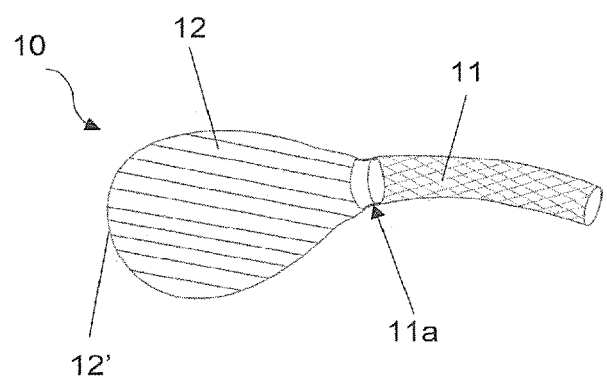
FIG. 5B is a schematic top down view of the device of FIG. 5A with a stent 11 and a deployable coaptation structure 12 extending from the inferior border 11a of the stent 11.
Figure 5C:
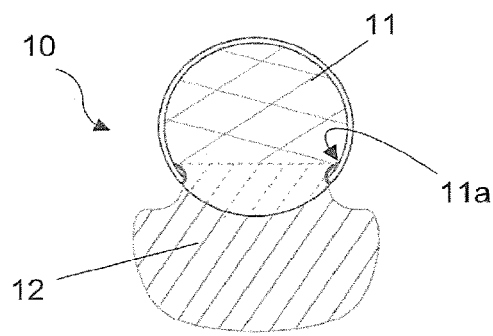
FIG. 5C is a schematic en-face view of a device of FIGS. 5A and 5B with a stent 11 and a deployable coaptation structure 12 extending from the inferior border 11a of the stent 11.
Figure 8:
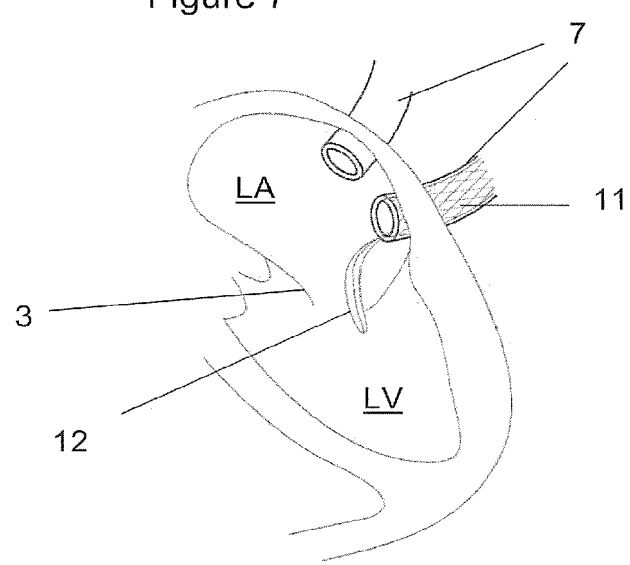
FIG. 8 is a schematic coronal view of a left side of the heart with an implanted device according to the embodiment as shown in FIGS. 5A to 5C. The device comprises an anchoring stent 11 implanted in a pulmonary vein 7 above the mitral valve 3, with a coaptation structure 12 extending in between the mitral valve leaflets.

FIG. 8 shows the cardiac valve repair device 10 of FIG. 5 implanted above a mitral valve 3 in the left atrium LA of a heart. The stent 11 of the device 10 is implanted into a pulmonary vein 7 and a neo-leaflet 12 extends from the stent 11 across the mitral valve and into the left ventricle LV. The neo-leaflet 12 preferably extends onto at least one mitral valve leaflet, and in between the mitral valve leaflets. In various embodiments, the device 10 comprises more than one upstream anchoring means, i.e. more than one stent 11, that may be implanted in more than one pulmonary vein 7 in the left atrium LA. The device 10 functions in the same manner as described above in relation to FIGS. 3 to 5, 14 and 15, for the tricuspid valve.

Figure 9A:
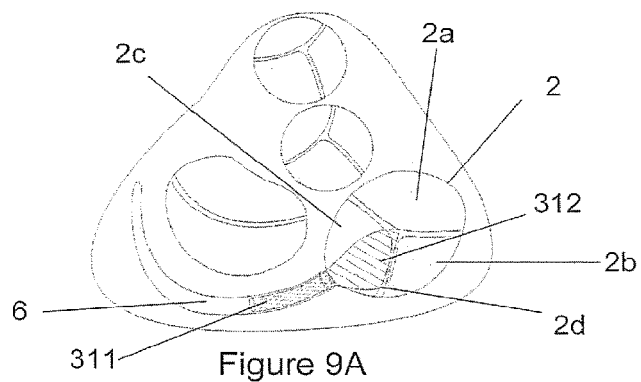
FIG. 9A is a schematic axial view of the heart with a different embodiment of a device (1) with an anchoring stent (2) and with a deployable valve repair structure shaped as a membrane wall structure (or a neo-leaflet) extending between the leaflets (31), here between the septal and posterior leaflets.
Figure 9B:
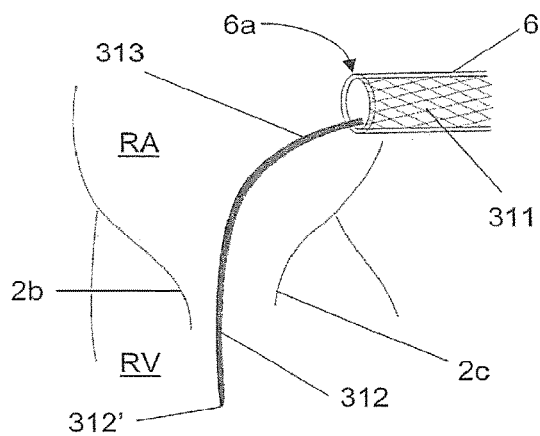
FIG. 9B is a schematic coronal section view of a left heart atrium and ventricle with an implanted cardiac valve repair device as shown in FIG. 9A. The device comprises a stent 311 deployed in the ostium 6a of blood vessel 6 (coronary sinus) located above the valve 2 and a deployable coaptation structure 312 extending between at least two of the valve leaflets 2b, 2c and functioning as a septum enhancing coaptation of the valve leaflets.

FIGS. 9A and 9B provides another embodiment of a cardiac valve repair device 310 comprises a stent 311 implanted in a coronary sinus 6, and a coaptation structure 312. The coaptation structure 312 is a membrane or a neo-leaflet 312 that is capable of extending between adjacent valve leaflets, e.g. posterior leaflet 2b and septal leaflet 2c, at the posteroseptal commissure 2d, into the right ventricle RV, where a free end 312' of the membrane or the neo-leaflet 312 is positioned downstream from the tricuspid valve 2, in the right ventricle RV. The membrane or the neo-leaflet 312 functions as a septum which enhances coaptation of the valve leaflets 2b, 2c. The membrane or the neo-leaflet 312 preferably extends across the tricuspid valve 2 via commissure 2d to act as a membrane wall structure on which the leaflets can coapt, thereby preventing their prolapse and flow regurgitation. Accordingly, the membrane or the neo-leaflet 312 may be inserted or slotted edgewise (or edge first) along the commissure 2d between the valve leaflets 2b, 2c so as to lie between the valve leaflets 2b, 2c in a manner resembling a dividing wall between the valve leaflets 2b, 2c along the commissure 2d.

Further, the membrane or the neo-leaflet 312 may be flexible. Accordingly, natural movements of the valve leaflets 2b, 2c may urge the membrane or the neo-leaflet 312 so as to move or bend or flex or displace the membrane or neo-leaflet 312 in order to shape or position or orient the membrane or the neo-leaflet 312 for adapting the membrane or the neo-leaflet 312 to promote coaptation with at least one of the valve leaflets 2a, 2b, 2c such that the gap is closed to prevent and/or minimize a backflow of blood. For example, the membrane or the neo-leaflet 312 may be bent or flexed into an "S" shaped profile, or tilted or rotated so as to slant or incline by the movement of the valve leaflets 2b, 2c. The changes in the shape or profile or position or orientation of the membrane or the neo-leaflet 312 along the commissure 2d may enhance the ability of the membrane or the neo-leaflet 312 to coapt with at least one of the valve leaflets 2a, 2b, 2c. As another example, the membrane or the neo-leaflet 312 may be moved or displaced or tilt or rotated so as to be laid over a surface of at least one heart valve leaflet of the patient's heart and extends beyond it to increase its length in a manner so as to serve as an extension of the at least one heart valve leaflet whereby the membrane or the neo-leaflet 312 may move in a similar manner as the at least one heart valve leaflet to coapt with at least one other heart valve leaflet of the patient's heart to prevent and/or minimize a backflow of blood.

Figure 10A:
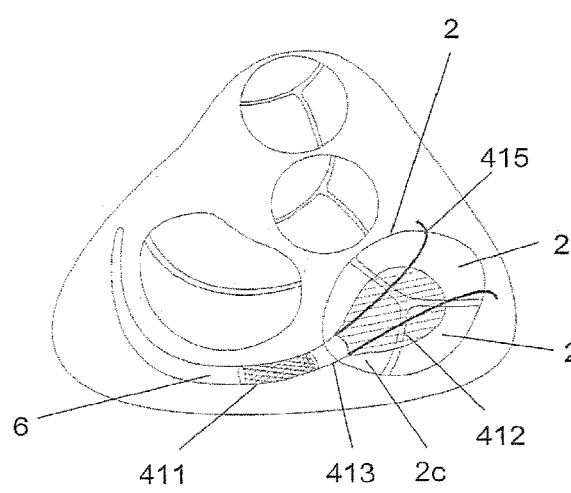
FIG. 10A is a schematic axial sectional view of a heart with a cardiac valve repair device according to an embodiment of the present invention, with a deployable backflow barrier 412 having two legs 415 extending between and superior to the leaflets of the tricuspid valve 2.
Figure 10B:
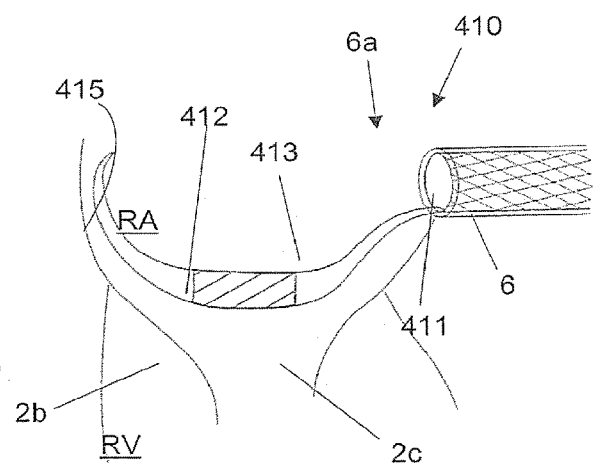
FIG. 10B is a schematic coronal section view of a right heart ventricle with the cardiac valve repair device as shown in FIG. 10A. The device includes a stent 411 deployed in the coronary sinus 6 located above the valve 2 and a backflow barrier 412 deployed in the right atrium above the valve leaflets and with legs 415 extending to the opposite side/wall of the right atrium.

FIGS. 10A and 10B provides another embodiment of a cardiac valve repair device 410 comprising a stent 411 implanted into a coronary sinus 6, tethers 413, a backflow barrier 412, and legs 415 (second upstream anchoring means). The legs 415 extend to the opposite side of the right atrium RA, i.e. opposite from the coronary sinus 6. The backflow barrier 412 is positioned by the tethers 413 and the legs 415 centrally above and close to the area of regurgitation (e.g. in between and superior to the valve leaflets) to prevent regurgitation of the blood flow in the defective valve during the cardiac cycle. The legs 415 maintain stability of the backflow barrier 412, which acts as a repair structure by preventing prolapse of defective valve leaflets.

In various embodiments, the backflow barrier 412 has substantially the same structure as a neo-leaflet (e.g. neo-leaflet 12) of the present invention, although the backflow barrier 412 does not coapt with the valve leaflets when in operation. In such embodiments, the backflow barrier 412 comprises a flexible structural support frame that is shaped like a leaflet or a flap, and a bioprosthetic tissue that is attached to the frame. The backflow barrier 412 is preferably flexible. Preferably, the backflow barrier 412 is substantially planar.

The legs 415 can extend from the tethers 413 or from the end (distal from the stent 411) of the backflow barrier 412 depending on the application and requirements. The legs 415 may be part of a unitary structure of the device 410 or a separate component attachable to the device 410. The ends of the legs 415 are shaped to engage/abut a wall of the atrium, which provides a resistive force to maintain the position of the device 410 and the backflow barrier 412 with respect to the tricuspid valve 2. In various embodiments, the ends of the legs 415 are configured to anchor to the wall of the atrium, for example the ends of the legs 415 comprise clamps that are adapted to pierce the atrial wall to anchor the device 410 in the atrium. The legs 415 may be made of the same material as the stent 411, tether 413 and/or the structural support frame of the backflow barrier 412. In various embodiments, the device 410 may comprise a single leg 415 or more than two legs 415. Preferably, the device 410 comprises at least one leg 415 as a second upstream anchoring means.

Figure 11:
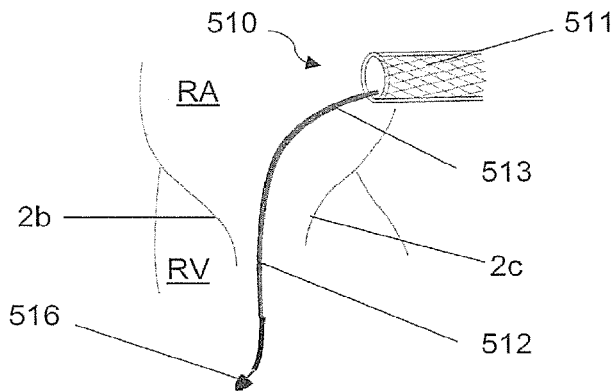
FIG. 11 is a schematic coronal sectional view of a right heart ventricle with a cardiac valve repair device according to an embodiment of the present invention. The device comprises a stent 511 deployed in a vessel located above the valve 2, a deployable coaptation structure 512 extending into the right ventricle RV and a downstream anchoring means 516 at the end of the coaptation structure 512.

FIG. 11 provides another embodiment of a cardiac valve repair device 510 comprising a stent 511 implanted into a coronary sinus, tethers 513, a neo-leaflet 512 that extends from the stent 511 via tethers 513 and a downstream anchoring means 516 distal from the stent 511. The downstream anchoring means 516 is connected to an end of the neo-leaflet 512 distal from the stent 511, and may be unitary with the neo-leaflet 512. In other embodiments where the downstream anchoring means 516 is a separate component from the neo-leaflet 512, the downstream anchoring means 516 is attachable to an end of the neo-leaflet 512 via means as described in the specification herein. A downstream connecting means may be used to connect the end of the neo-leaflet 512 and the downstream anchoring means 516.

The neo-leaflet 512 extends across the tricuspid valve 2 into the right ventricle RV, in between the tricuspid valve leaflets, where the downstream anchoring means 516 is configured to anchor to a tissue site in the right ventricle RV, downstream from the tricuspid valve 2. The downstream anchoring means 516 cooperates with the stent 511 and tethers 513 to maintain the neo-leaflet 512 at the intended location between the valve leaflets. Maintenance of the coaptation structure at the intended location between the valve leaflets preferably avoids the coaptation structure (for example where the coaptation structure is a balloon) from getting struck in an offset position in the commissures between the valve leaflets, which can result in leakage of the valve.

Additionally, the downstream anchoring means 516 functions as a restraint in the prevention of prolapse of the neo-leaflet 512 into the right atrium RA, during right ventricular systole. The downstream anchoring means 516 may be anchored at an endocardial or pericardial tissue site. The downstream anchoring means 516 can comprise tines, barbs, screws and/or clamps that are capable of piercing the cardiac wall for anchorage.

Figure 12A:
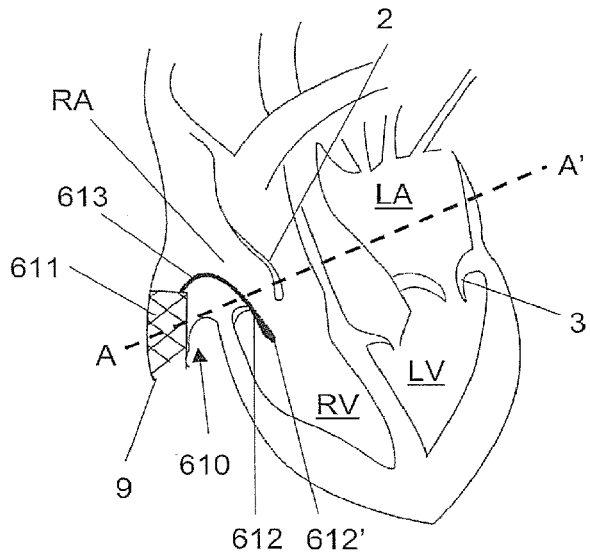
FIG. 12A is a schematic coronal view of a heart with an implanted cardiac valve repair device according to an embodiment of the present invention, where the device comprises a stent 611 anchored to the inferior vena cava 9 and a deployable coaptation structure 612 from the stent 611 into the right ventricle RV.
Figure 12B:
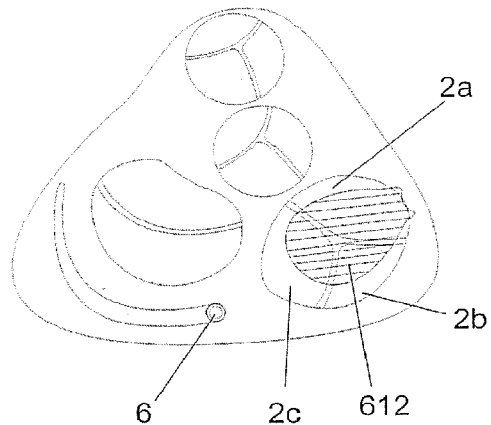
FIG. 12B is a schematic axial sectional view of the heart of FIG. 12A along axis A-A'.

FIGS. 12A and 12B provides another embodiment of a cardiac valve repair device 610 comprising a stent 611 implanted in the inferior vena cava 9, and a neo-leaflet 612 that extends from the stent 611 into the right ventricle RV across the tricuspid valve 2, such that a free end 612' of the neo-leaflet 612 locates in the right ventricle RV, downstream of the tricuspid valve 2. The device 610 can comprise tethers that lengthens the device 610 to extend the neo-leaflet 612 into the right ventricle RV. In the present embodiment, the neo-leaflet 612 extends onto the anterior leaflet 2a of the tricuspid valve 2.

In various embodiments, the device can comprise an additional upstream anchoring means that anchors to a tissue site upstream from the heart valve, for example, the device 610 can comprise a second stent that is implantable into the superior vena cava, and cooperates with the stent 611 in the inferior vena cava to secure and position the neo-leaflet 612 at an intended location with respect to the tricuspid valve. In other various embodiments, the stent 611 may be implanted in the superior vena cava instead of the inferior vena cava.

Figure 13:
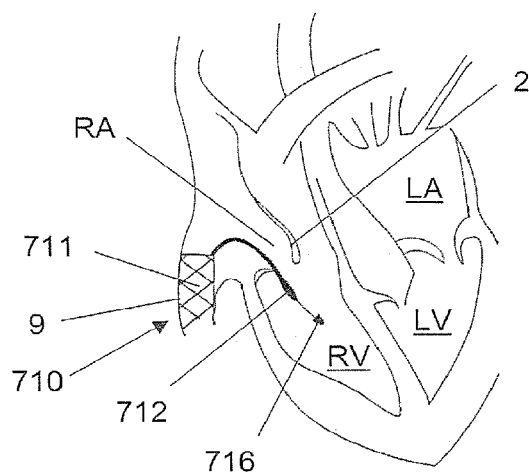
FIG. 13 is a schematic coronal view of a heart with an implanted cardiac valve repair device according to an embodiment of the present invention, where the device comprises a stent 711 anchored to the inferior vena cava 9, a deployable coaptation structure 712 from the stent 711 into the right ventricle RV and a downstream anchoring means 716 at the end of the coaptation structure 712.

FIG. 13 provides another embodiment of a cardiac valve repair device 710 comprising a stent 711 implanted in the inferior vena cava 9, a neo-leaflet 712 that extends from the stent 711 into the right ventricle RV across the tricuspid valve 2, and a downstream anchoring means 716 distal from the stent 711 and extending from an end of the neo-leaflet 712.

The neo-leaflet 712 extends into the right ventricle RV in between the tricuspid valve leaflets, where the downstream anchoring means 716 is configured to anchor to a tissue site in the right ventricle RV, downstream from the tricuspid valve 2. The downstream anchoring means 716 cooperates with the stent 711 to maintain the neo-leaflet 712 at the intended location between the valve leaflets. Maintenance of the coaptation structure at the intended location between the valve leaflets preferably avoids the coaptation structure (for example where the coaptation structure is a balloon) from getting struck in an offset position in the commissures between the valve leaflets, which can result in leakage of the valve.

Additionally, the downstream anchoring means 716 functions as a restraining means in the prevention of prolapse of the neo-leaflet 712 into the right atrium RA, during right ventricular systole. The downstream anchoring means 716 may be anchored at an endocardial or pericardial tissue site. The downstream anchoring means 716 can comprise tines, barbs and/or clamps that are capable of piercing the cardiac wall for anchorage.

Figure 16A:
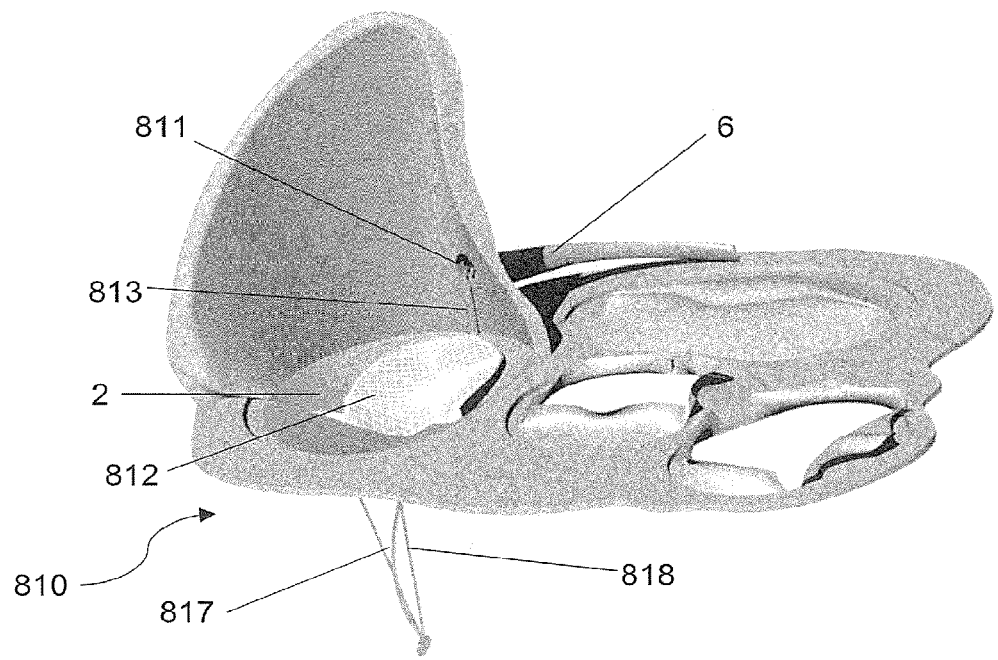
FIG. 16A is a perspective view of a 3D reconstruction of an implanted cardiac valve repair device according to an embodiment of the present invention. The device comprises a stent 811 anchored at the coronary sinus 6 with a coaptation structure 812 extending into the right ventricle RV. The device also comprises a stabilizing structure 817 connected to the coaptation structure 812 via stabilizing tethers 818.
Figure 16B:
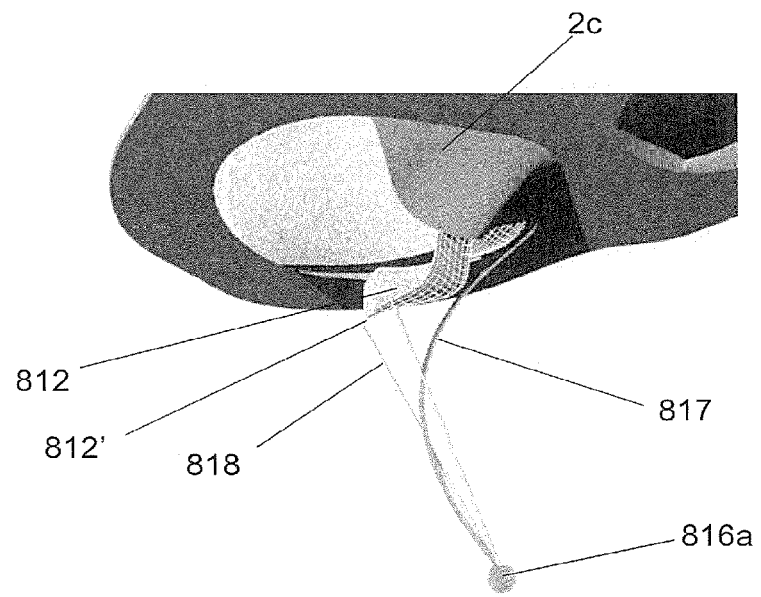
FIG. 16B is a perspective view of the device of FIG. 16A, viewed from the right ventricle.

FIGS. 16A and 16B provide another embodiment of a cardiac valve repair device 810 comprising a stent 811 implanted into a coronary sinus 6, a neo-leaflet 812 having a distal free end 812' extending into the right ventricle across the tricuspid valve 2, a tether 813 connecting an end border of the stent 811 to a proximal end of the neo-leaflet 812, and a stabilizing means 817 that extends further into the right ventricle with respect to the free end 812'. The neo-leaflet 812 preferably extends onto at least one tricuspid valve leaflet. The stabilizing means 817 extends from the tether 813 and/or the stent 811, below an inferior surface of the neo-leaflet 812 and into the right ventricle, across the tricuspid valve 2. In various embodiments, the inferior surface of the neo-leaflet 812 or a part thereof is connected to the stabilizing means 817.

The stabilizing means 817 comprises a wire or a plurality of wires formed from a shape memory metal alloy that is flexible, e.g. nitinol-titanium. The stabilizing means 817 is attached via one or more stabilizing tethers 818 to the neo-leaflet 812 at a portion substantially close to or at the free end 812', such that the stabilizing means 817 forms an extension of the free end 812'. The stabilizing means 817 is shaped (e.g. curved downwards towards a ventricular apex) to maintain the free end 812' of the neo-leaflet 812 in the right ventricle during the cardiac cycle, by maintaining a restraining force in the direction downstream from the valve. Therefore, during a ventricular systole, the stabilizing means 817 exerts a counter force in an opposite direction of the blood flow against the valve so as to prevent prolapse of the neo-leaflet 812. The stabilizing means 817 exerts this tensional/restraining force via stabilizing tethers 818. The stabilizing tethers 818 function like chordae tendineae which prevent the eversion and prolapse of the neo-leaflet 812, especially during systole, by becoming tense and pulling the neo-leaflet 812, holding it in a closed coaptation position with the other valve leaflets.

The stabilizing means 817 comprises a weighted end 816a distal from the neo-leaflet 812 that preferably assists via gravity, in the extension of the stabilizing means 817 in the ventricle. The weighted end 816a may be a free end which moves freely within the ventricle, or an end that abuts against a ventricular wall to aid in the positioning of the neo-leaflet 812 at an intended location with respect to the heart valve. The stabilizing tethers 818 are attached to the weighted end 816a. In other embodiments, the stabilizing tethers 818 are attached to other portions of the stabilizing means 817. In other various embodiments, the weighted end 816a is a downstream anchoring means operable to anchor to a tissue site downstream with respect to the valve.

In other various embodiments, the stabilizing means 817 is attached to the free end 812' of the neo-leaflet 812, such that the stabilizing means 817 can be considered an extension of the neo-leaflet 812 and the weighted end 816a can be considered an extension of the free end 812'. In such embodiments, the stabilizing means 817 may not comprise stabilizing tethers 818 since the weighted end 816a would be sufficient to maintain the free end 812' of the neo-leaflet 812 in the ventricle.

Methods of Delivery, Deployment and Implantation of the Cardiac Valve Repair Device FIGS. 17A to 17F illustrate steps of a method for delivering, deploying and implanting a cardiac valve repair device 10 according to the embodiment shown in FIGS. 3 to 5, 14 and 15. The cardiac valve repair device 10 comprises an anchoring device, a stent 11, and a neo-leaflet 12 which are separate components that are adapted to be connected together in vivo.

Figure 17A:
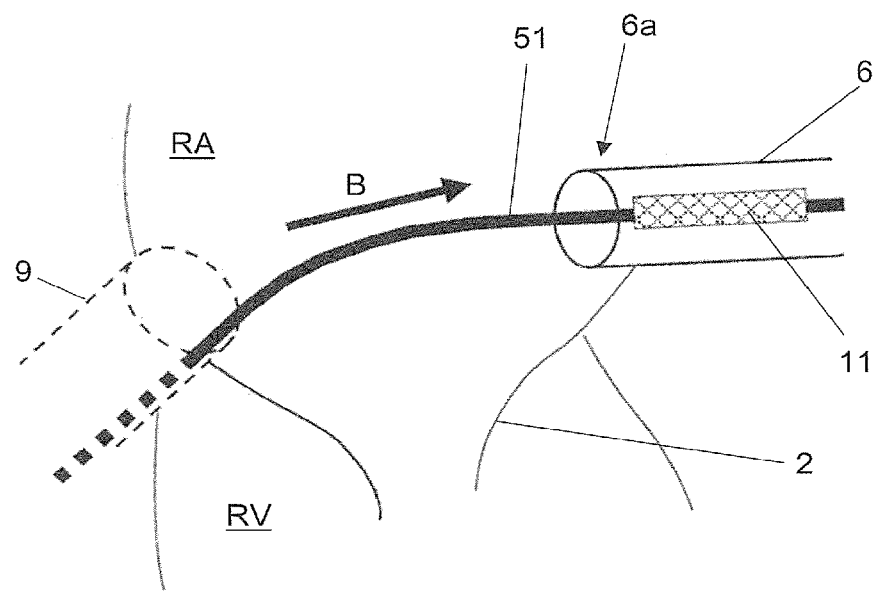
FIGS. 17A to 17F illustrate steps of a method for delivering, deploying and implanting a cardiac valve repair device according to an embodiment of the present invention, where a stent 11 is implanted in the coronary sinus of a right heart atrium and a coaptation structure 12 extends across a tricuspid valve, from the stent 11.
Figure 17B:
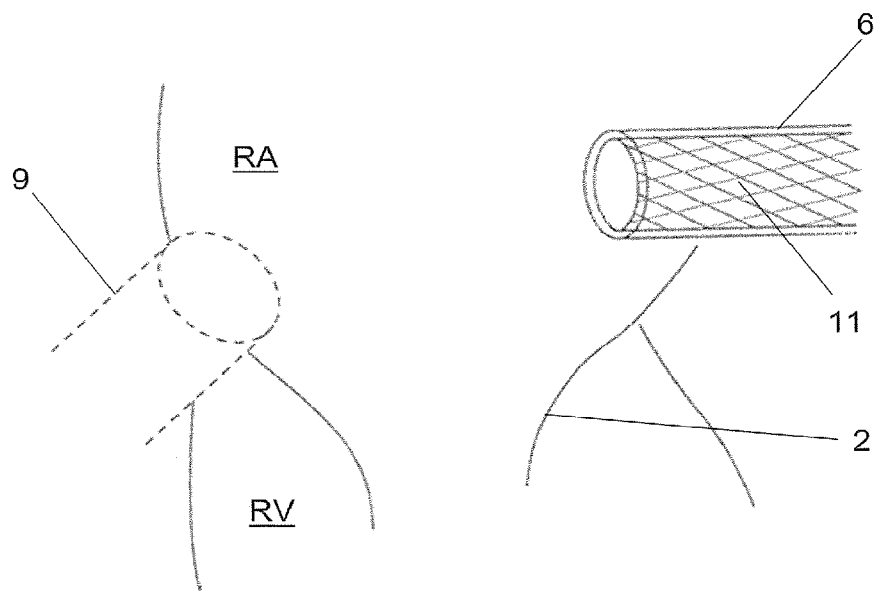

Referring to FIG. 17A, the stent 11 is delivered via the inferior vena cava 9 in a direction B to the coronary sinus 6 of a right heart atrium RA by a first delivery catheter 51. Access to the right heart atrium RA may be from the femoral vein, internal jugular or subclavian vein. A guide wire (not shown) may be used to guide the first delivery catheter 51 to the intended location in the patient's heart. The stent 11 is preferably crimped/compressed and may be enveloped (wholly or in part) by the delivery catheter, such that upon reaching the intended location, the stent 11 is unsheathed for the purposes of anchoring to an upstream tissue site. The stent 11 is preferably crimped/compressed during transcatheter delivery to allow for relatively smooth tracking of the system through the blood vessels to an intended tissue site. Further, it allows the stent 11 to fit within a lumen of a blood vessel (e.g. coronary sinus) that is intended to be the upstream tissue site for anchorage. The stent 11 is positioned by the first delivery catheter 51 within the coronary sinus 6 such that upon anchorage, one end of the stent 11 is contiguous with the ostium 6a of the coronary sinus 6, as shown in FIG. 17B.

Upon reaching the coronary sinus 6, the stent 11 is radially expanded by for example a balloon catheter, to urge and secure the stent 11 against and engage the luminal wall of the coronary sinus 6. The engagement of the stent 11 against the luminal wall of the coronary sinus 6 provides a resistive force that anchors the stent 11 within the coronary sinus 6. When expanded, the stent 11 is substantially rigid to prevent collapse of the stent 11 during operation of the cardiac valve repair device 10. After the stent 11 is anchored to the coronary sinus 6, the stability of the stent 11 may be tested by tug testing which includes tugging on the stent 11 to check if the stent 11 will dislodge from the coronary sinus 6. The first delivery catheter 51 may be fully retracted for subsequent steps of the method to take place.

Figure 17C:
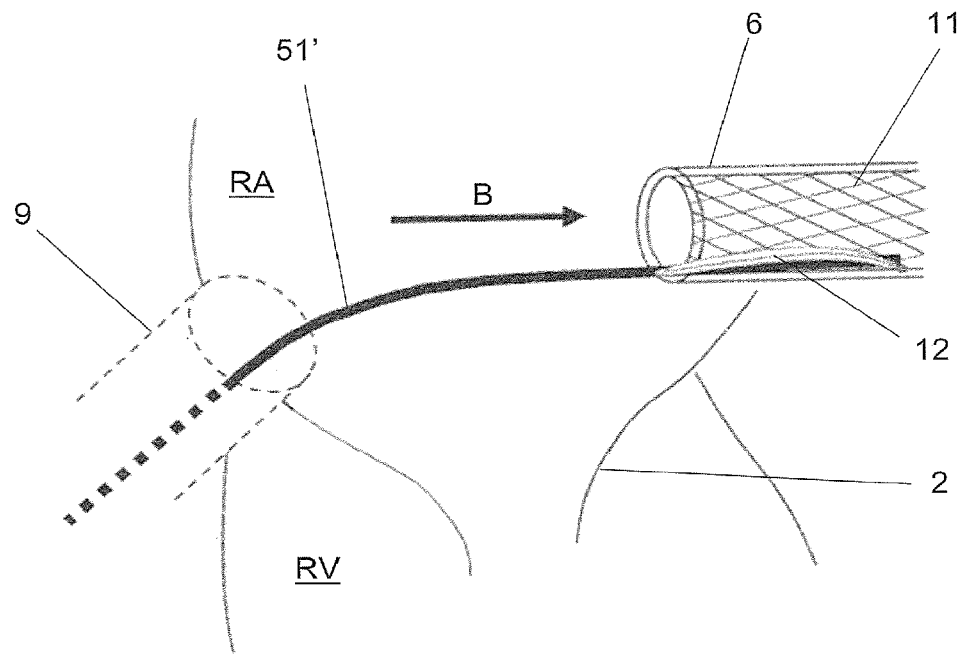
Figure 17D:
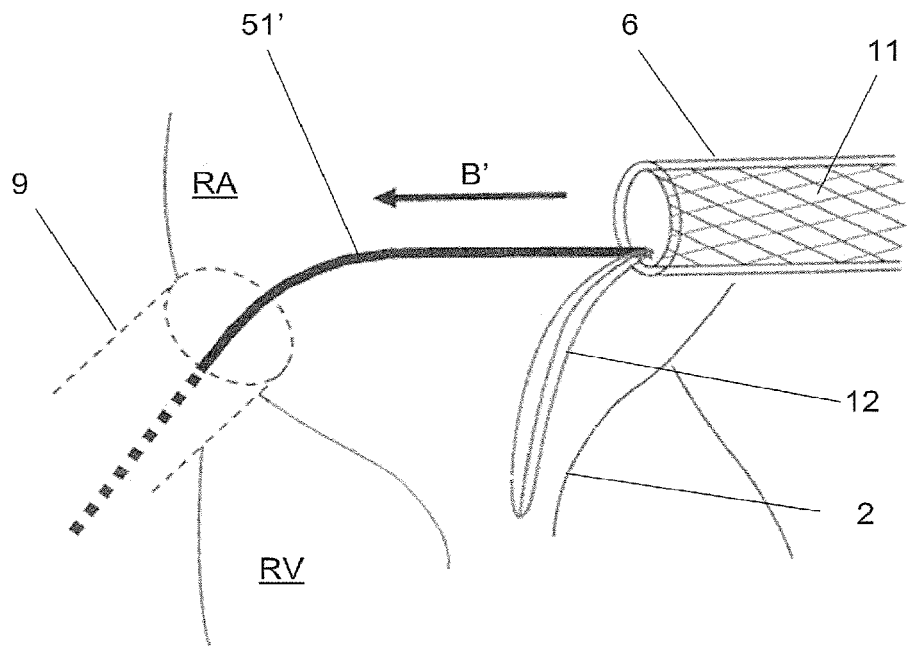

A second delivery catheter 51' delivers the neo-leaflet 12 in a direction B via the inferior vena cava 9 to the coronary sinus 6 where the stent 11 is anchored (FIG. 17C). A guide wire (not shown) may be used to guide the second delivery catheter 51' to the coronary sinus 6. The neo-leaflet 12 is preferably compressible/crimpable and may be enveloped (wholly or in part) by the delivery catheter, such that upon reaching the intended location, the neo-leaflet 12 is unsheathed and unfurled for deployment. The neo-leaflet 12 is preferably crimped/compressed during transcatheter delivery to allow for relatively smooth tracking of the system through the blood vessels to the intended location. In various embodiments, the neo-leaflet 12 is releasably attached to an end of the second delivery catheter 51'. The second delivery catheter 51' extends substantially within the coronary sinus 6 in the direction B to contact the neo-leaflet 12 with the interior surface of the stent 11, which can assist in the positioning of the neo-leaflet 12 for attachment with the stent 11.

Figure 17E:
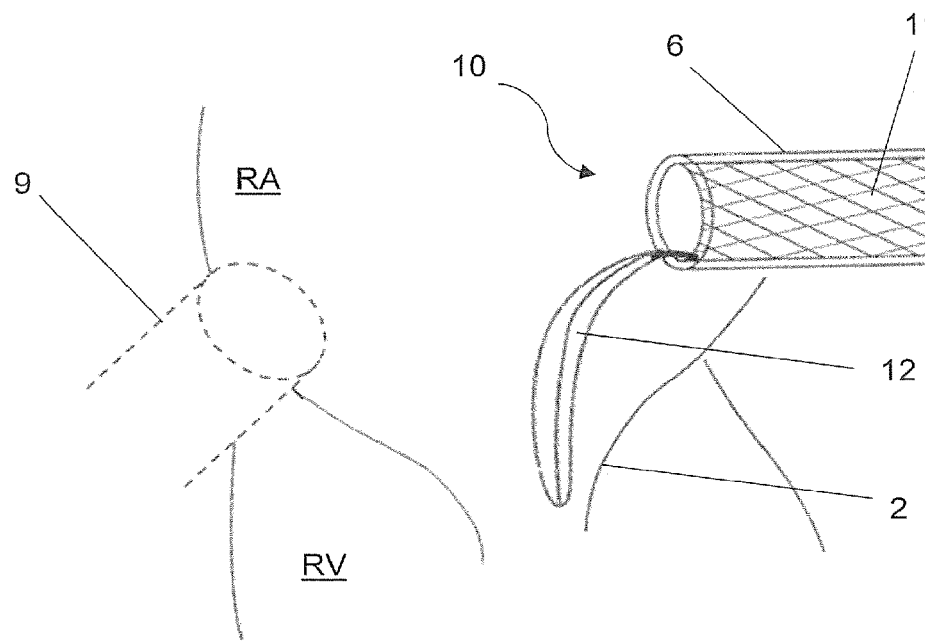
Figure 17F:
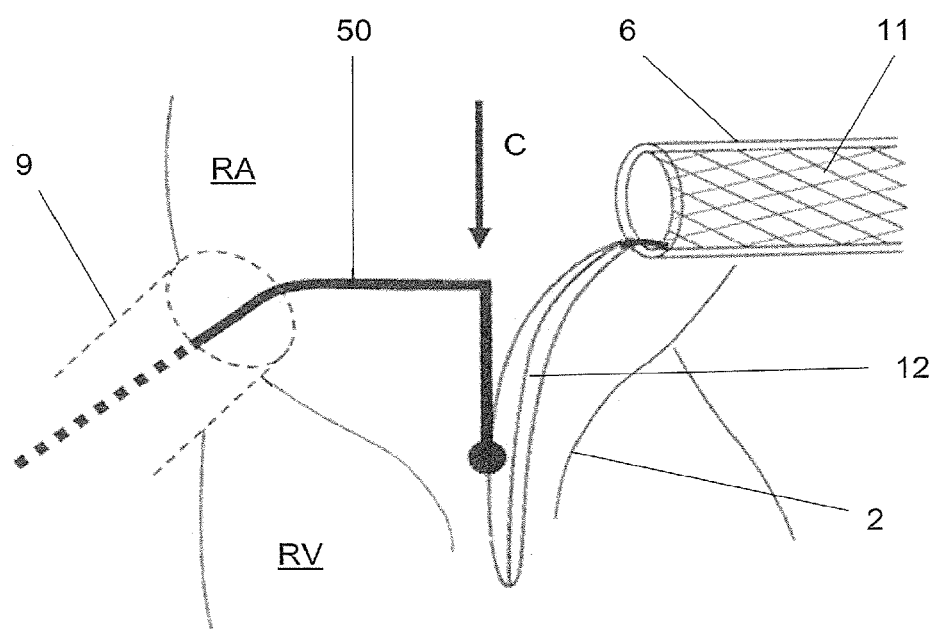

The second delivery catheter 51' is thereafter moved in a direction B' (FIG. 17D) to position one end of the neo-leaflet 12 with an inferior border of the stent 11, where the neo-leaflet 12 is attached to the inferior border of the stent 11 via a connecting means (e.g. bioadhesives, stitchings, hooks and screws) as described herein. As shown in FIG. 17E, the second delivery catheter 51' is fully retracted and neo-leaflet 12 extends from the stent 11. In various embodiments, the neo-leaflet 12 naturally extends across the tricuspid valve 2 for coaptation with at least one valve leaflet to prevent, reduce and/or minimize a backflow of blood. In other various embodiments and as shown in FIG. 17F, a guide wire 50 is advanced in a downstream direction C to urge the neo-leaflet 12 to position across the tricuspid valve 2. For example, the neo-leaflet 12 may extend across the tricuspid valve 2 via the centre of the tricuspid valve annulus, or a commissure between two tricuspid valve leaflets, or on and/or laid over a surface of a tricuspid valve leaflet, etc.

Further, the method for delivering, deploying and implanting the cardiac valve repair device as illustrated in FIG. 17A to 17F is also applicable for the embodiment as shown in FIGS. 9A and 9B, except that the membrane or the neo-leaflet 312 is position to extend across the tricuspid valve 2 via the commissure 2d between two tricuspid valve leaflets 2b, 2c.

FIGS. 18A to 18D illustrate steps of a method for delivering, deploying and implanting a cardiac valve repair device 610 according to the embodiment shown in FIGS. 12A and 12B. The cardiac valve repair device 610 comprises a stent 611 and a neo-leaflet 612 which are unitary, or separate components that are adapted to be connected together ex vivo.

Figure 18A:
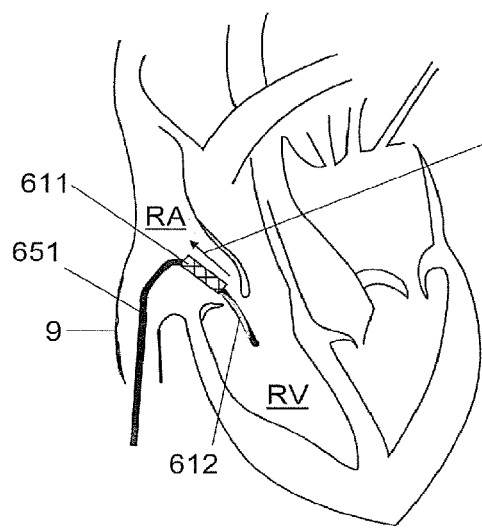
FIGS. 18A to 18D illustrate steps of a method for delivering, deploying and implanting a cardiac valve repair device according to another embodiment of the present invention, where a stent 611 is implanted in an inferior vena cava and a coaptation structure 612 extends across a tricuspid valve, from the stent 611.
Figure 18B:
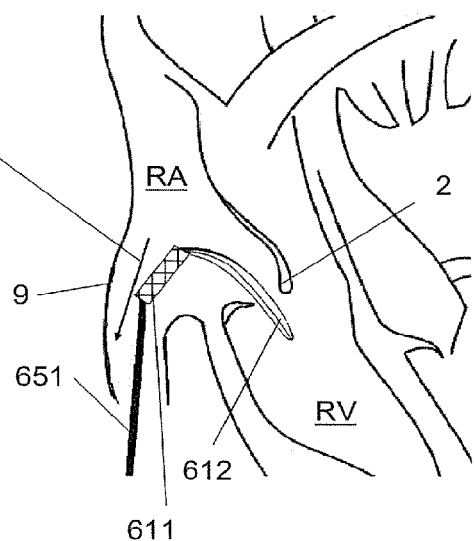
Figure 18C:
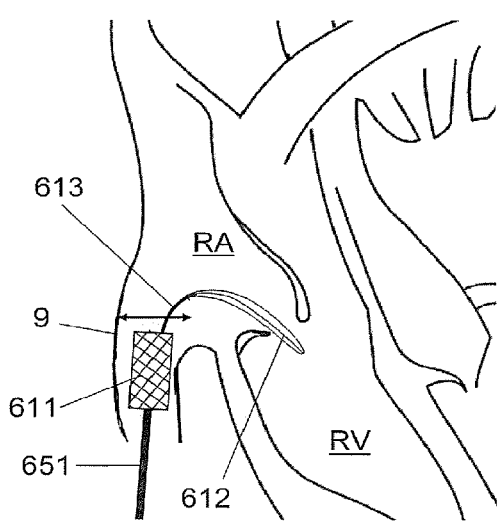
Figure 18D:
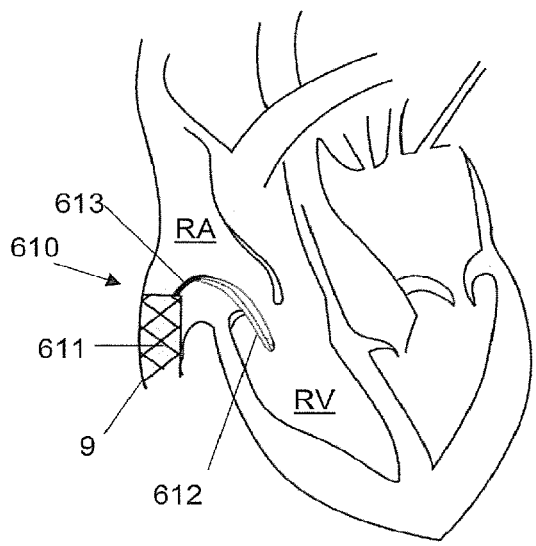

Referring to FIG. 18A, the cardiac valve repair device 610 is delivered via the inferior vena cava 9 the right side of a heart by a delivery catheter 651. The device 610 is preferably compressible/crimpable and may be enveloped (wholly or in part) by the delivery catheter, such that upon reaching the intended location, the device 610 is unsheathed. The delivery catheter 651 is advanced to the right ventricle RV such that an end of the delivery catheter 651 is positioned within the right ventricle RV, so that upon unsheathing the device 610 (e.g. via an obturator), a free end of the neo-leaflet 612 may be positioned within the right ventricle RV and the neo-leaflet 612 extends across the tricuspid valve 2. For example, the neo-leaflet 612 may extend across the tricuspid valve 2 via the centre of tricuspid valve annulus, or a commissure between two tricuspid valve leaflets, or on and/or laid over a surface of a tricuspid valve leaflet, etc. The delivery catheter 651 is retracted in the direction D to first expose and unsheathe the neo-leaflet 612 and thereafter the stent 611 (FIG. 18B).

The delivery catheter 651 continues moving in the direction D to locate the stent 611 substantially within the inferior vena cava 9. The stent 611 is connected/attached to the neo-leaflet 612 via tethers 613 to provide sufficient length between the stent 611 and the neo-leaflet 612 for the neo-leaflet 612 to extend across the tricuspid valve 2 during operation of the device 610. In various embodiments where the neo-leaflet 612 is sufficiently long, one end of the neo-leaflet 612 is connected/attached to one end of the stent 611 (e.g. with bioadhesives), without the use of tethers. When the stent 611 is located substantially within the inferior vena cava 9, the stent 611 is radially expanded by for example a balloon catheter, to urge and secure the stent 611 against and engage the luminal wall of the inferior vena cava 9. The engagement of the stent 611 against the luminal wall of the inferior vena cava 9 provides a resistive force that anchors the stent 611 within the inferior vena cava 9. When expanded, the stent 611 is substantially rigid to prevent collapse of the stent 611 during operation of the cardiac valve repair device 610. After the stent 611 is anchored to the inferior vena cava 9, the stability of the stent 611 may be tested by tug testing which includes tugging on the stent 611 to check if the stent 611 will dislodge from the inferior vena cava 9. The delivery catheter 651 is then fully retracted to complete the implantation of the device 610 (FIG. 18D), where the neo-leaflet 612 extends across the tricuspid valve 2.

Further, the method for delivering, deploying and implanting the cardiac valve repair device as illustrated in FIG. 18A to 18D is also applicable for the embodiment as shown in FIGS. 9A and 9B, except that the membrane or the neo-leaflet 312 is position to extend across the tricuspid valve 2 via the commissure 2*d* between two tricuspid valve leaflets 2*b*, 2*c*.

FIGS. 19A to 19D illustrate steps of another method for delivering, deploying and implanting a cardiac valve repair device 610 according to the embodiment shown in FIGS. 12A and 12B. The cardiac valve repair device 610 comprises a stent 611 and a neo-leaflet 612 which are separate components that are adapted to be connected together in vivo.

Figure 19A:
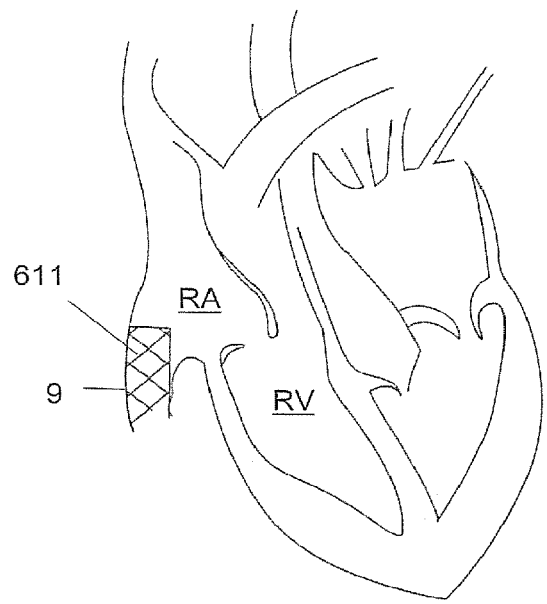
FIGS. 19A to 19D illustrate steps of another method for delivering, deploying and implanting a cardiac valve repair device according to the embodiment of the present invention according to FIGS. 18A to 18D, where a stent 611 is implanted in an inferior vena cava and a coaptation structure 612 extends across a tricuspid valve, from the stent 611.

Referring to FIG. 19A, the stent 611 is delivered to the inferior vena cava 9 by a first delivery catheter (not shown). Upon reaching the inferior vena cava 9, the crimped/compressed stent 611 is radially expanded by for example a balloon catheter, to urge the stent 611 against and engage the luminal wall of the inferior vena cava 9. The engagement of the stent 611 against the luminal wall of the inferior vena cava 9 provides a resistive force that anchors the stent 611 within the inferior vena cava 9. When expanded, the stent 611 is substantially rigid to prevent collapse of the stent 611 during operation of the cardiac valve repair device 610. After the stent 611 is anchored to the inferior vena cava 9, the stability of the stent 611 may be tested by tug testing which includes tugging on the stent 611 to check if the stent 611 will dislodge from the inferior vena cava 9.

Figure 19B:
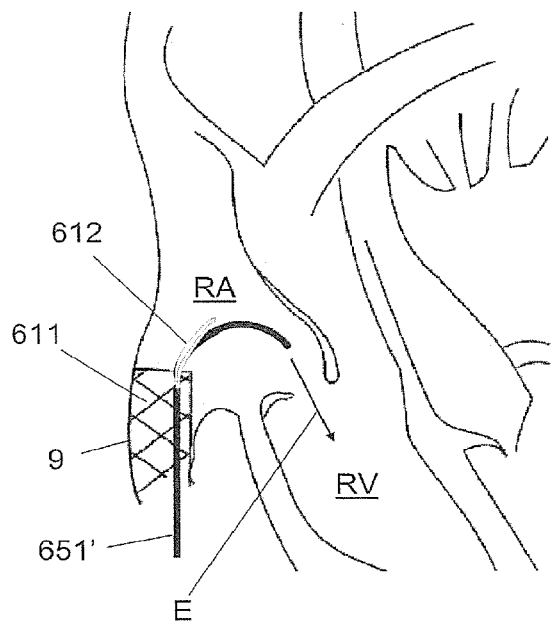
Figure 19C:
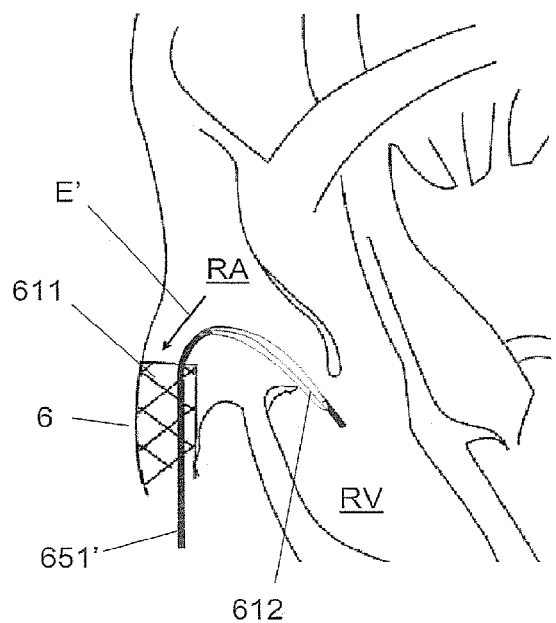
Figure 19D:
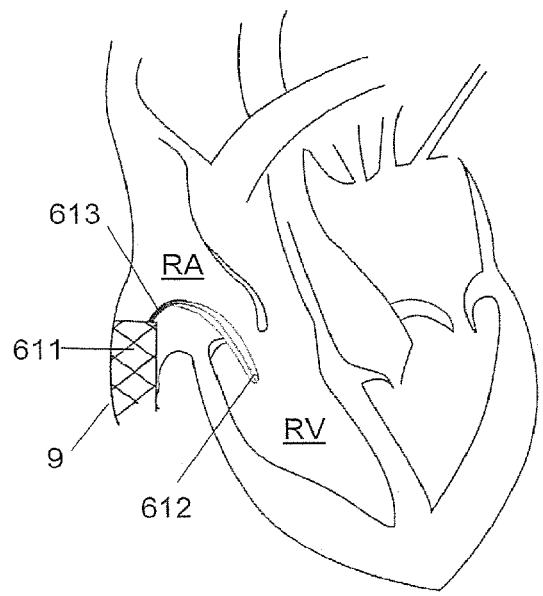

A second delivery catheter 651' delivers in a direction E, the neo-leaflet 612 via the inferior vena cava 9 and through the stent 611, to the right heart atrium RA and the right heart ventricle RV (FIGS. 19B and 19C). The delivery catheter 651' is advanced to the right ventricle RV such that an end of the delivery catheter 651' is positioned within the right ventricle RV, so that upon unsheathing the neo-leaflet 612 (e.g. by an obturator), a free end of the neo-leaflet 612 may be positioned within the right ventricle RV and the neo-leaflet 612 may extend across the tricuspid valve 2. For example, the neo-leaflet 612 may extend across the tricuspid valve 2 via the centre of the tricuspid valve annulus, or a commissure between two tricuspid valve leaflets, or on and/or laid over a surface of a tricuspid valve leaflet, etc. The delivery catheter 651 is retracted in the direction E' to expose and unsheathe the neo-leaflet 612 (FIG. 19C), and to bring one end of the neo-leaflet 612 close to the stent 611.

After the neo-leaflet 612 has been positioned to extend across the tricuspid valve 2, the neo-leaflet 612 is connected to the stent 611 via tethers 613. The tethers 613 provide sufficient length between the stent 611 and the neo-leaflet 612 for the neo-leaflet 612 to extend across the tricuspid valve 2 during operation of the device 610. In various embodiments where the neo-leaflet 612 is sufficiently long, one end of the neo-leaflet 612 is connected/attached to one end of the stent 611 (e.g. with bioadhesives), without the use of tethers.

Further, the method for delivering, deploying and implanting the cardiac valve repair device as illustrated in FIG. 19A to 19D is also applicable for the embodiment as shown in FIGS. 9A and 9B, except that the membrane or the neo-leaflet 312 is position to extend across the tricuspid valve 2 via the commissure 2*d* between two tricuspid valve leaflets 2*b*, 2*c*.

Figures 20A, 20B:
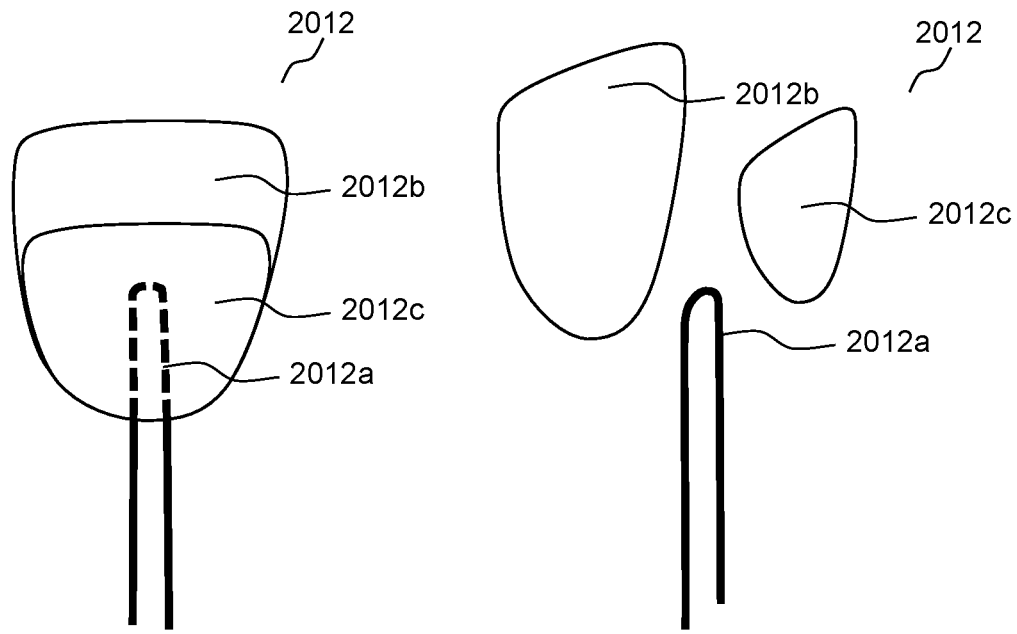
FIGS. 20A and 20B show schematic drawings of an example embodiment of a neo-leaflet 2012 according to various embodiments, where the neo-leaflet 2012 includes two layers/sheets of material 2012*b*, 2012*c* (e.g. bioprosthetic or biocompatible material) attached to the structural support frame 2012*a*.

FIGS. 20A and 20B show schematic drawings of an example embodiment of a neo-leaflet 2012 according to various embodiments. As shown, the neo-leaflet 2012 may include two layers/sheets of material 2012*b*, 2012*c* (e.g. bioprosthetic or biocompatible material) attached to the structural support frame 2012*a*. The two layers/sheets of material 2012*b*, 2012*c* may be of different shape and sizes. The two layers/sheets of material 2012*b*, 2012*c* may be respectively attached to two opposite sides of the structural support frame 2012*a* to cover the structural support frame 2012*a*. Accordingly, the neo-leaflet 2012 may have different (or uneven or non-uniform) thickness along its length. The length of the neo-leaflet 2012 may be measured from a base of the neo-leaflet 2012 to a tip of the neo-leaflet 2012 opposite and/or farthest from the base.

Figures 21A, 21B:
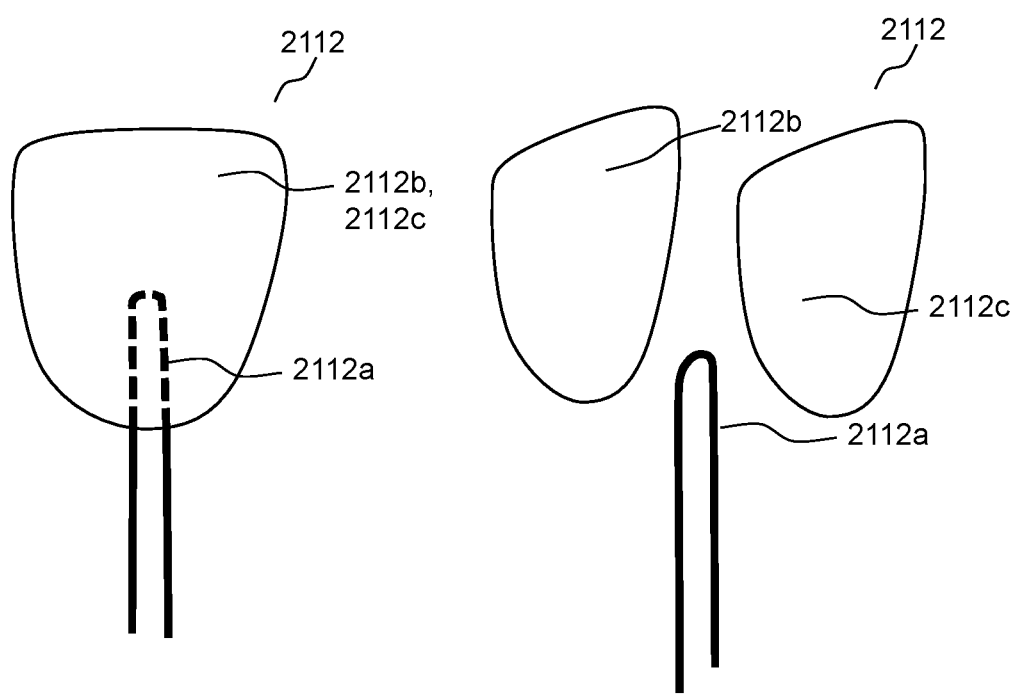
FIGS. 21A and 21B show schematic drawings of an example embodiment of a neo-leaflet 2112 according to various embodiments, where the neo-leaflet 2112 includes two layers/sheets of material 2112*b*, 2112*c* (e.g. bioprosthetic or biocompatible material) attached to the structural support frame 2112*a*.

FIGS. 21A and 21B show schematic drawings of an example embodiment of a neo-leaflet 2112 according to various embodiments. As shown, the neo-leaflet 2112 may include two layers/sheets of material 2112*b*, 2112*c* (e.g. bioprosthetic or biocompatible material) attached to the structural support frame 2112*a*. The two layers/sheets of material 2112*b*, 2112*c* may be of different shape and sizes. The two layers/sheets of material 2112*b*, 2112*c* may be respectively attached to two opposite sides of the structural support frame 2112*a* to cover the structural support frame 2112*a*. Accordingly, the neo-leaflet 2112 may have a uniform thickness along its length. The length of the neo-leaflet 2112 may be measured from a base of the neo-leaflet 2112 to a tip of the neo-leaflet 2112 opposite and/or farthest from the base.

Figure 22A:
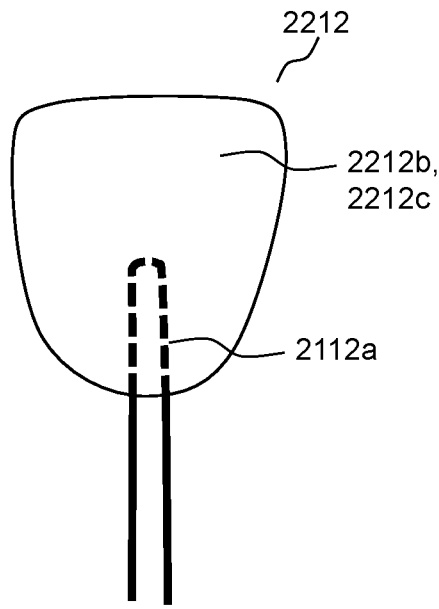
FIGS. 22A and 22B show schematic drawings of an example embodiment of a neo-leaflet 2212 according to various embodiments, where the neo-leaflet 2212 includes three layers/sheets of material 2212*b*, 2212*c*, 2212*d* (e.g. bioprosthetic or biocompatible material) attached to the structural support frame 2212*a*.
Figure 22B:
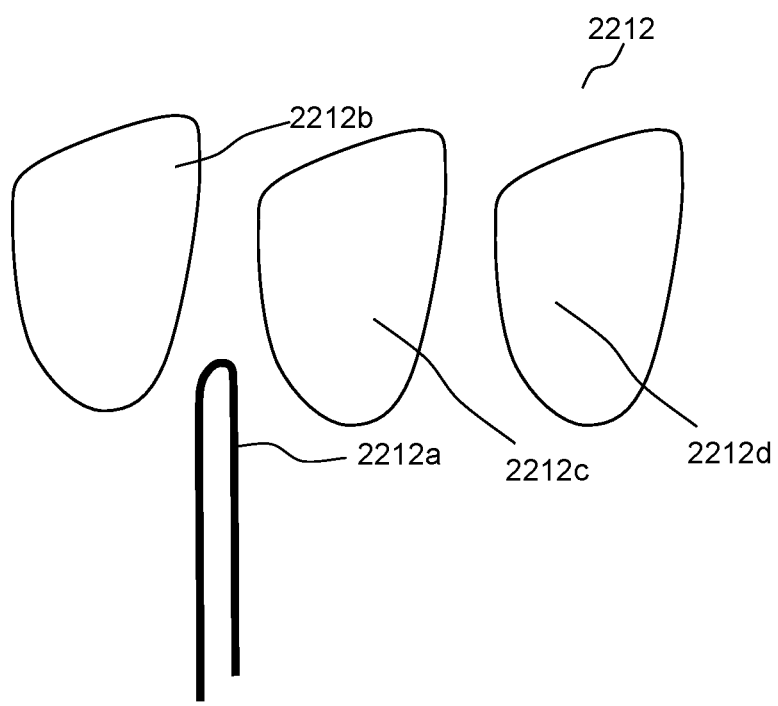

FIGS. 22A and 22B show schematic drawings of an example embodiment of a neo-leaflet 2212 according to various embodiments. As shown, the neo-leaflet 2212 may include three layers/sheets of material 2212*b*, 2212*c*, 2212*d* (e.g. bioprosthetic or biocompatible material) attached to the structural support frame 2212*a*. The three layers/sheets of material 2212*b*, 2212*c* may be of different shape and sizes. One layer/sheet of material 2212*b* may be attached to a first side of the structural support frame 2212*a* and the other two layers/sheets of material 2212*c*, 2212*d* may be attached to a second side of the structural support frame 2212*a* so as to cover the structural support frame 2212*a*. Accordingly, the neo-leaflet 2212 may have a uniform thickness along its length. The length of the neo-leaflet 2212 may be measured from a base of the neo-leaflet 2212 to a tip of the neo-leaflet 2212 opposite and/or farthest from the base.

It should be understood that while certain variants of the present invention are illustrated and described herein, the invention is defined by the description and is not to be limited to the specific embodiments described and shown in the figures. For example, according to the invention is also conceivable that:

the upstream anchoring means described herein as a stent can be made of another anchoring expandable structure or a screw;

the coaptation structure deployed inside a patient's heart valve to restore valve function can be a spherical or tubular member or a prosthetic replacement valve;

the device of the present invention can be applied to valve anatomies other than the tricuspid valve, for example the mitral valve;

the device of the present invention can comprise methods of delivering, deploying and anchoring/implanting the neo-leaflet/flap to restore valve function and coaptation of the valve leaflets, other than the methods described herein; and various components of the cardiac valve repair device can be combined with one another even if not explicitly disclosed, for example, the device can comprise a superior vena cava anchoring stent, a neo-leaflet that extends onto the anterior leaflet of a tricuspid valve and into the right ventricle, and a stabilizing means that extends further into the right ventricle with respect to the neo-leaflet, where the stabilizing means maintains a free end of the neo-leaflet in the ventricle.

REFERENCES

1. Tang G H, David T E, Singh S K, Maganti M D, Armstrong S, Borger M A. Tricuspid valve repair with an annuloplasty ring results in improved long-term outcomes. Circulation 2006; 114:I577-81.
2. McCarthy P M, Bhudia S K, Rajeswaran J, et al. Tricuspid valve repair: durability and risk factors for failure. The Journal of thoracic and cardiovascular surgery 2004; 127:674-85.
3. Ghanta R K, Chen R, Narayanasamy N, et al. Suture bicuspidization of the tricuspid valve versus ring annuloplasty for repair of functional tricuspid regurgitation: midterm results of 237 consecutive patients. The Journal of thoracic and cardiovascular surgery 2007; 133:117-26.
4. Singh J P, Evans J C, Levy D, et al. Prevalence and clinical determinants of mitral, tricuspid, and aortic regurgitation (the Framingham Heart Study). The American journal of cardiology 1999; 83:897-902.
5. Nath J, Foster E, Heidenreich P A. Impact of tricuspid regurgitation on long-term survival. Journal of the American College of Cardiology 2004; 43:405-9.
6. Izumi C, Iga K, Konishi T. Progression of isolated tricuspid regurgitation late after mitral valve surgery for rheumatic mitral valve disease. The Journal of heart valve disease 2002; 11:353-6.
7. Porter A, Shapira Y, Wurzel M, et al. Tricuspid regurgitation late after mitral valve replacement: clinical and echocardiographic evaluation. The Journal of heart valve disease 1999; 8:57-62.
8. Matsunaga A, Duran C M. Progression of tricuspid regurgitation after repaired functional ischemic mitral regurgitation. Circulation 2005; 112:I453-7.

The invention claimed is:

1. A device for cardiac valve repair, the device comprising:
 a stent adapted to anchor to at least one tissue site, the at least one tissue site located upstream with respect to a heart valve of a patient; and
 a neo-leaflet arranged to extend from the stent, the neo-leaflet comprising a free end distal from the stent, wherein the neo-leaflet comprises
  a flexible structural support frame providing flexibility to the neo-leaflet and
  a bioprosthetic or biocompatible material attached to the structural support frame,
 wherein the neo-leaflet is operable to extend across the heart valve and locate the free end downstream from the heart valve, wherein the neo-leaflet is inserted across the heart valve via a commissure in between two heart valve leaflets of the patient's heart for coapting with at least one heart valve leaflet of the patient's heart to prevent and/or minimize a backflow of blood.

2. The device according to claim 1, wherein the upstream tissue site is a blood vessel.

3. The device according to claim 1, wherein the heart valve is a tricuspid valve,
 wherein the stent is adapted to:
  (a) anchor at a coronary sinus of the patient's heart; or
  (b) anchor at an inferior vena cava of the patient; or
  (c) anchor at the superior vena cava of the patient.

4. The device according to claim 1, wherein the heart valve is a mitral valve and the stent is adapted to anchor at a pulmonary vein of the patient's heart.

5. The device according to claim 1, further comprising tethers, screws, mechanical locks, hooks, magnets, sutures, fabric, plication, crimps, staples, rivets, or adhesives adapted to connect the stent and the neo-leaflet.

6. The device according to claim 1, wherein the device comprises clamps, hooks, tines, barbs, screws or bio-adhesives extending from the free end of the neo-leaflet, wherein the clamps, hooks, tines, barbs, screws or bio-adhesives are adapted to anchor at a downstream tissue site with respect to the heart valve of the patient.

7. The device according to claim 6, wherein the downstream tissue site is an endocardial or pericardial tissue site of a heart ventricle of the patient.

8. The device according to claim 1, wherein the device comprises a stabilizing structure adapted to extend across the heart valve of the patient, and wherein the stabilizing structure is configured to maintain a downstream location of the free end of the neo-leaflet wherein the stabilizing structure comprises:
 (a) a weighted free end; or
 (b) one or more stabilizing tether adapted to connect the stabilizing structure to the neo-leaflet.

9. The device according to claim 1, wherein the neo-leaflet is of a petal shape.

10. The device according to claim 1, wherein the neo-leaflet comprises two or more layers of bioprosthetic or biocompatible material attached to the structural support frame from two opposite sides of the structural support frame.

11. The device according to claim 10, wherein the two or more layers of bioprosthetic or biocompatible material are of the same shape or sizes.

12. The device according to claim 10, wherein the two or more layers of bioprosthetic or biocompatible material are of different shape and sizes.

13. The device according to claim 10, wherein the neo-leaflet has a thickness of 0.1 mm to 6 mm.

14. A method of implanting a device for cardiac valve repair in a patient's heart, the method comprising the steps of:
 a) delivering a device for cardiac valve repair to the patient's heart, the device comprising a stent and a neo-leaflet arranged to extend from the stent, the neo-leaflet comprising a free end distal from the stent, wherein the neo-leaflet comprises a flexible structural support frame providing flexibility to the neo-leaflet and a bioprosthetic or biocompatible material attached to the structural support frame;
 b) anchoring the stent to at least one tissue site in the patient's heart, the at least one tissue site located upstream with respect to a heart valve of the patient's heart;
 c) deploying the neo-leaflet to extend across the heart valve to locate the free end of the neo-leaflet downstream from the heart valve by inserting the neo-leaflet across the heart valve via a commissure in between two heart valve leaflets of the patient's heart for coapting with at least one heart valve leaflet of the patient's heart to prevent and/or minimize a backflow of blood.

15. The method according to claim 14, wherein the method further comprises the step of testing and verifying the stability of the stent.

16. The method according to claim 14, wherein the method comprises anchoring the stent at a coronary sinus of a right atrium of the patient's heart, and deploying the neo-leaflet such that the free end of the neo-leaflet extends into the right heart ventricle of the patient and the neo-leaflet coapts with at least one tricuspid valve leaflet of the patient's heart.

17. The method according to claim 14, wherein the method comprises anchoring the stent at an inferior vena cava of the patient, and deploying the neo-leaflet such that the free end of the neo-leaflet extends into a right heart ventricle of the patient and the neo-leaflet coapts with at least one tricuspid valve leaflet of the patient's heart.

18. The method according to claim 14, wherein the method comprises anchoring the stent at a pulmonary vein of a left atrium of the patient's heart, and deploying the neo-leaflet such that the free end of the neo-leaflet extends into the left heart ventricle of the patient and the neo-leaflet coapts with at least one mitral valve leaflet of the patient's heart.

19. A method of implanting a device for cardiac valve repair in a patient's heart, the method comprising the steps of:
  a) delivering a device for cardiac valve repair to the patient's heart, the device comprising a stent and a single neo-leaflet arranged to extend from the stent, the neo-leaflet having a shape of one heart valve leaflet of the patient's heart or part thereof, the neo-leaflet comprising a free end distal from the stent, wherein the neo-leaflet comprises a flexible structural support frame providing flexibility to the neo-leaflet;
  b) anchoring the stent to at least one tissue site in the patient's heart, the at least one tissue site located upstream with respect to a heart valve of the patient's heart;
  c) deploying the neo-leaflet to extend across the heart valve to locate the free end of the neo-leaflet downstream from the heart valve by inserting the neo-leaflet across the heart valve via a commissure in between two heart valve leaflets of the patient's heart for coapting with at least one heart valve leaflet of the patient's heart to prevent and/or minimize a backflow of blood.

20. The method according to claim 19, wherein the method comprises anchoring the stent at a coronary sinus of a right atrium of the patient's heart, and deploying the neo-leaflet such that the free end of the neo-leaflet extends into the right heart ventricle of the patient and the neo-leaflet extends across the heart valve via a commissure in between two tricuspid valve leaflets of the patient's heart.

* * * * *